US010207421B1

(12) United States Patent
Weinschenk

(10) Patent No.: US 10,207,421 B1
(45) Date of Patent: Feb. 19, 2019

(54) AUTOMATED MULTI-HEADED SAW AND METHOD FOR LUMBER

(71) Applicant: Steven R. Weinschenk, Rochester, MN (US)

(72) Inventor: Steven R. Weinschenk, Rochester, MN (US)

(73) Assignee: Wein Holding LLC, Rochester, MN (US)

( * ) Notice: Subject to any disclaimer, the term of this patent is extended or adjusted under 35 U.S.C. 154(b) by 0 days.

(21) Appl. No.: 15/658,026

(22) Filed: Jul. 24, 2017

Related U.S. Application Data

(60) Provisional application No. 62/495,830, filed on Sep. 26, 2016.

(51) Int. Cl.
| | |
|---|---|
| *B27B 5/36* | (2006.01) |
| *B27B 31/06* | (2006.01) |
| *B27B 27/04* | (2006.01) |

(52) U.S. Cl.
CPC .............. *B27B 5/36* (2013.01); *B27B 27/04* (2013.01); *B27B 31/06* (2013.01)

(58) Field of Classification Search
CPC ........... B27B 5/36; B27B 27/04; B27B 31/06
See application file for complete search history.

(56) References Cited

U.S. PATENT DOCUMENTS

| | | | | |
|---|---|---|---|---|
| 1,804,764 | A * | 5/1931 | Grant ...................... | B27B 31/06 116/202 |
| 1,916,567 | A * | 7/1933 | Grant ...................... | B27B 31/06 116/281 |
| 2,510,471 | A * | 6/1950 | Horstkotte .............. | B27B 31/06 83/508.3 |

(Continued)

FOREIGN PATENT DOCUMENTS

CN          202899636 U      4/2013

OTHER PUBLICATIONS

Weinmann Holzbausystemtechnik GMBH, "WHP 100 Robotic Material Handling Portal", "Structural Building Components Magazine, downloaded from: http://www.sbcmag.info/sites/default/files/Archive/2008/sep/0809_cc.pdf", Sep./Oct. 2008.

(Continued)

*Primary Examiner* — Sean M Michalski
(74) *Attorney, Agent, or Firm* — Charles A. Lemaire; Lemaire Patent Law Firm, P.L.L.C.

(57) ABSTRACT

A system including a gantry structure; a first and a second saw head movable along at least part of the length of the gantry structure; and a first and a second lumber support also movable along corresponding lengths of the gantry structure. A controller moves the first saw head and first lumber support adjacent a first location along a board and moves the second saw head and second lumber support adjacent a second location along a board, and operates the first and second saw heads to cut first and second ends off the board. The controller then moves the saw heads and the lumber supports relative to the board to third and fourth locations and operates the first and second saw heads to cut third and fourth end pieces off. The saw heads and lumber supports optionally move together and rotate around respective vertical axes to enable angled board cuts.

20 Claims, 17 Drawing Sheets

(56) References Cited

U.S. PATENT DOCUMENTS

| | | | |
|---|---|---|---|
| 2,806,492 A * | 9/1957 | Becker | B27B 31/06 |
| | | | 83/520 |
| 3,124,181 A * | 3/1964 | Clemans | B27B 27/04 |
| | | | 269/150 |
| 3,815,738 A | 6/1974 | Sweet et al. | |
| 4,139,035 A | 2/1979 | Bystedt et al. | |
| 4,196,648 A | 4/1980 | Jones et al. | |
| 4,867,213 A | 9/1989 | Bolton et al. | |
| 4,909,112 A | 3/1990 | Rosenthal | |
| 4,951,215 A | 8/1990 | Scherer | |
| 4,992,949 A | 2/1991 | Arden | |
| 5,335,790 A | 8/1994 | Geiger et al. | |
| 5,564,573 A | 10/1996 | Palm et al. | |
| 6,170,163 B1 | 1/2001 | Bordignon et al. | |
| 6,923,614 B2 | 8/2005 | Aylsworth | |
| 7,463,368 B2 | 12/2008 | Morden et al. | |
| 7,621,053 B2 | 11/2009 | Bianchin | |
| 7,801,637 B2 | 9/2010 | Sander | |
| 7,950,316 B2 * | 5/2011 | Koskovich | B27B 5/205 |
| | | | 269/269 |
| 8,010,216 B2 | 8/2011 | Roise | |
| 8,079,579 B2 | 12/2011 | Fredrickson et al. | |
| 8,782,878 B2 | 7/2014 | Morden et al. | |
| 8,919,001 B2 * | 12/2014 | Le Mer | B63B 9/00 |
| | | | 33/286 |
| 8,960,244 B1 * | 2/2015 | Aylsworth | B27B 31/00 |
| | | | 144/245.5 |
| 9,316,506 B2 | 4/2016 | Aspen | |
| 9,369,632 B2 | 6/2016 | Short | |
| 10,080,003 B2 | 9/2018 | Tone | |
| 2005/0013472 A1 | 1/2005 | Gauthier | |
| 2005/0027389 A1 | 2/2005 | Hadaway et al. | |
| 2008/0223768 A1 | 9/2008 | Ahrens | |
| 2008/0297740 A1 | 12/2008 | Huynh et al. | |
| 2010/0201702 A1 | 8/2010 | Franik et al. | |
| 2014/0341444 A1 | 11/2014 | Hou et al. | |
| 2015/0054792 A1 | 2/2015 | Kuki | |
| 2017/0050334 A1 | 2/2017 | Aylsworth | |
| 2017/0057113 A1 | 3/2017 | Aylsworth | |
| 2017/0217022 A1 | 8/2017 | Aylsworth | |
| 2017/0274489 A1 | 9/2017 | Baratta | |
| 2017/0305029 A1 | 10/2017 | Aylsworth | |
| 2018/0001508 A1 | 1/2018 | Aylsworth | |

OTHER PUBLICATIONS

Weinmann Holzbausystemtechnik GMBH, "Carpentry machines WBS and WBZ", "Downloaded from internet: http://www.homag.com/fileadmin/product/houseconstruction/brochures/weinmann-carpentry-machines-WBS-and-WBZ-english.pdf", May 2016, Publisher: Publication at least as early May 2016.

Mereen-Johnson, LLC, "Mereen-Johnson Rip Optimizing Systems (internet web page)", "Downloaded from internet page: http://www.mereen-johnson.com/content/mereen-johnson-gang-rip-saw-optimizing-systems", possibly Sep. 2014, pp. 1-3.

Mereen-Johnson, LLC, "Rip Navigator Tracker Rip Optimizing System", "Downloaded from internet page: http://www.mereen-johnson.com/sites/default/files/2017-06/Rip%20Nav%20Tracker%20Multi%20page%20brochure.pdf", Sep. 2014, pp. 1-2.

Mereen-Johnson, LLC, "Rip Navigator Scout Rip Optimizing System", "Downloaded from internet page: http://www.mereen-johnson.com//sites/default/files/Rip%20Nav%20Scout%20Multi%20page%20brochure.pdf", Sep. 2014, pp. 1-3.

* cited by examiner

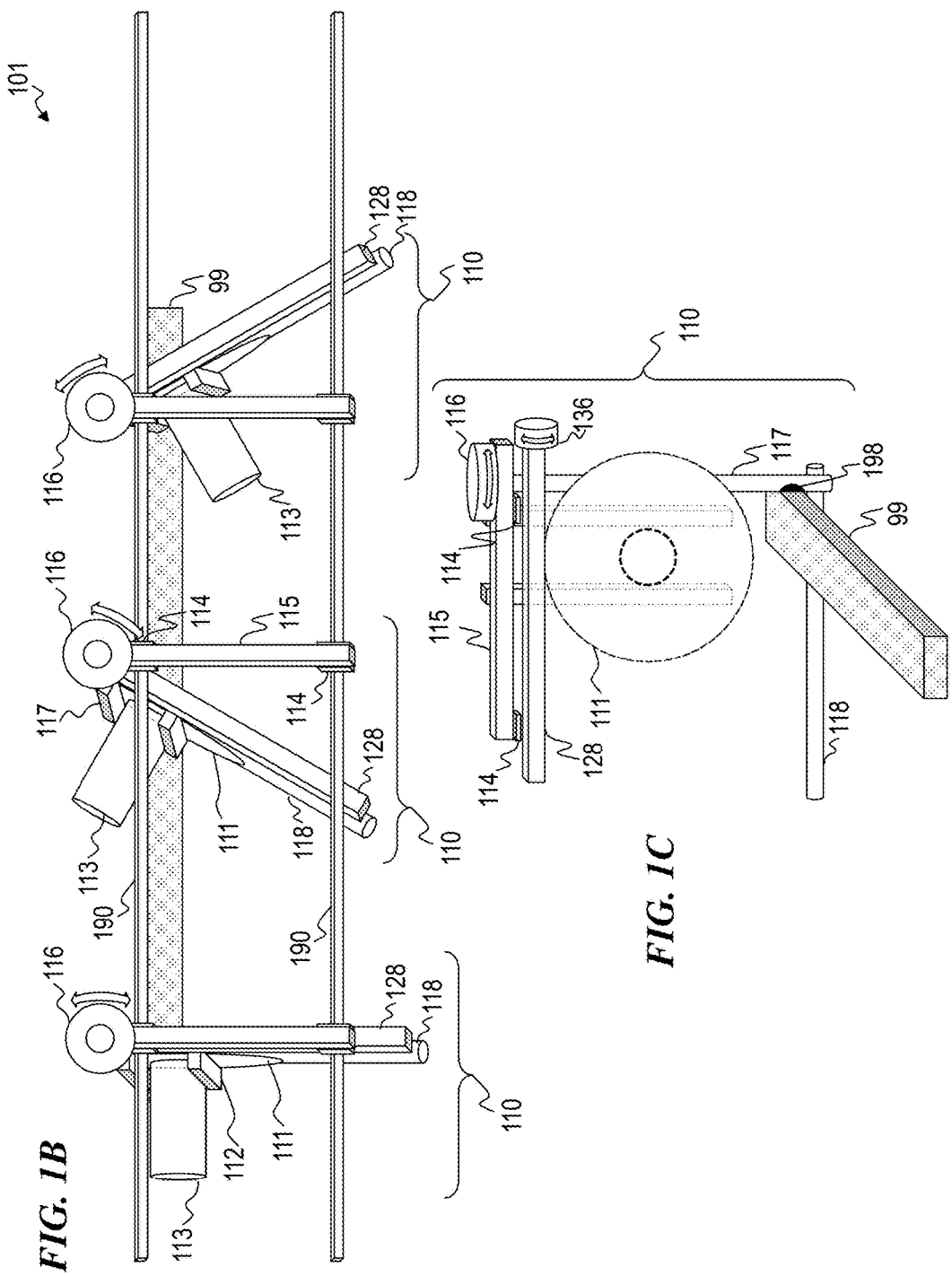

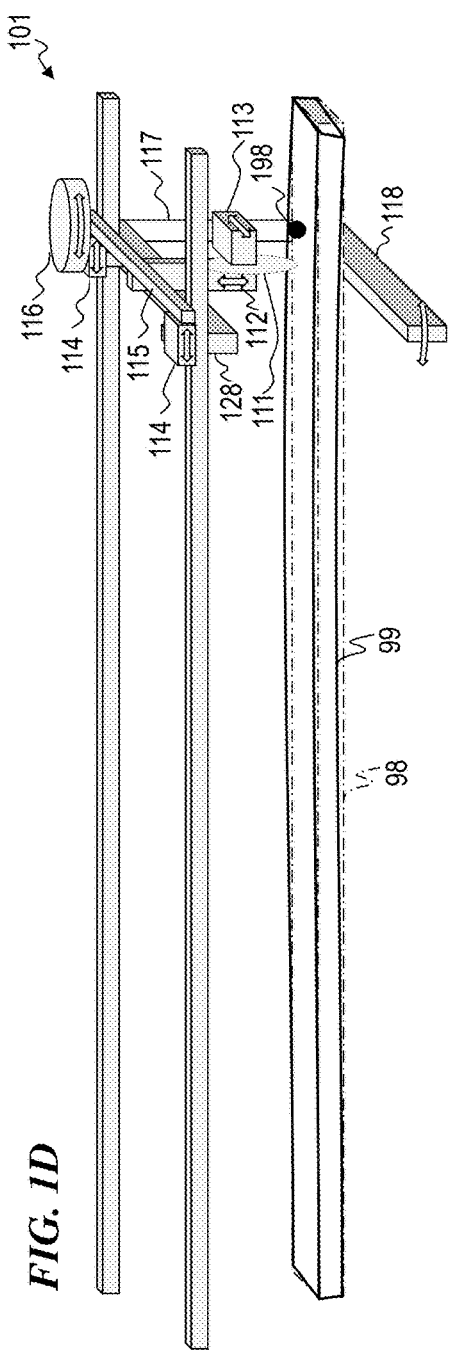
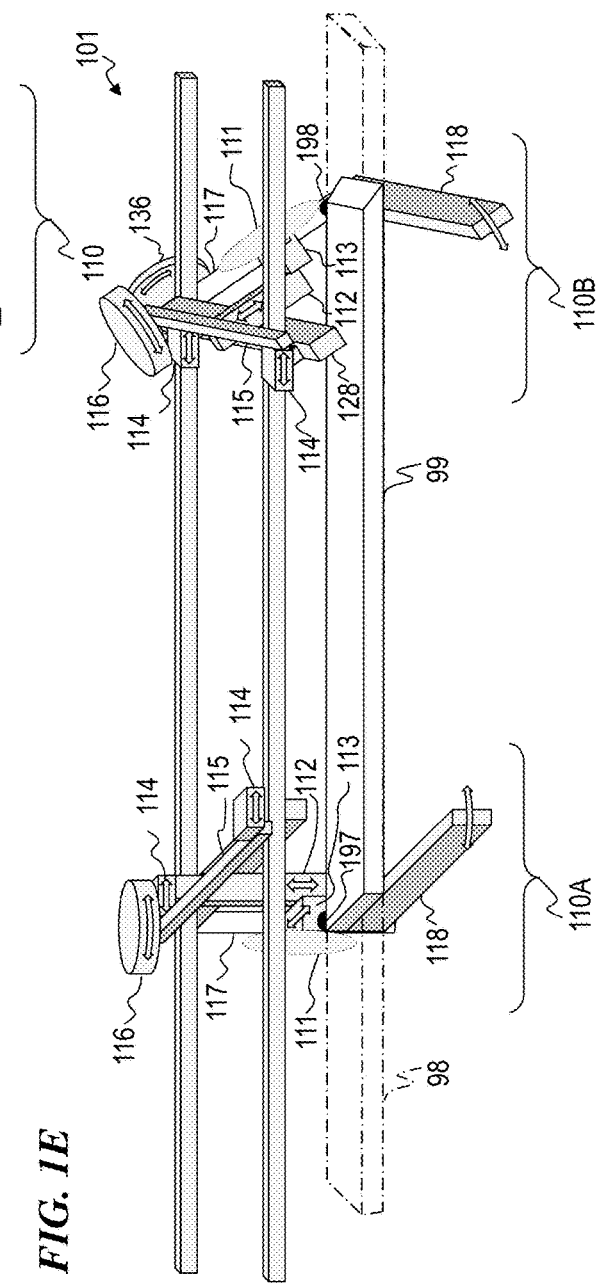

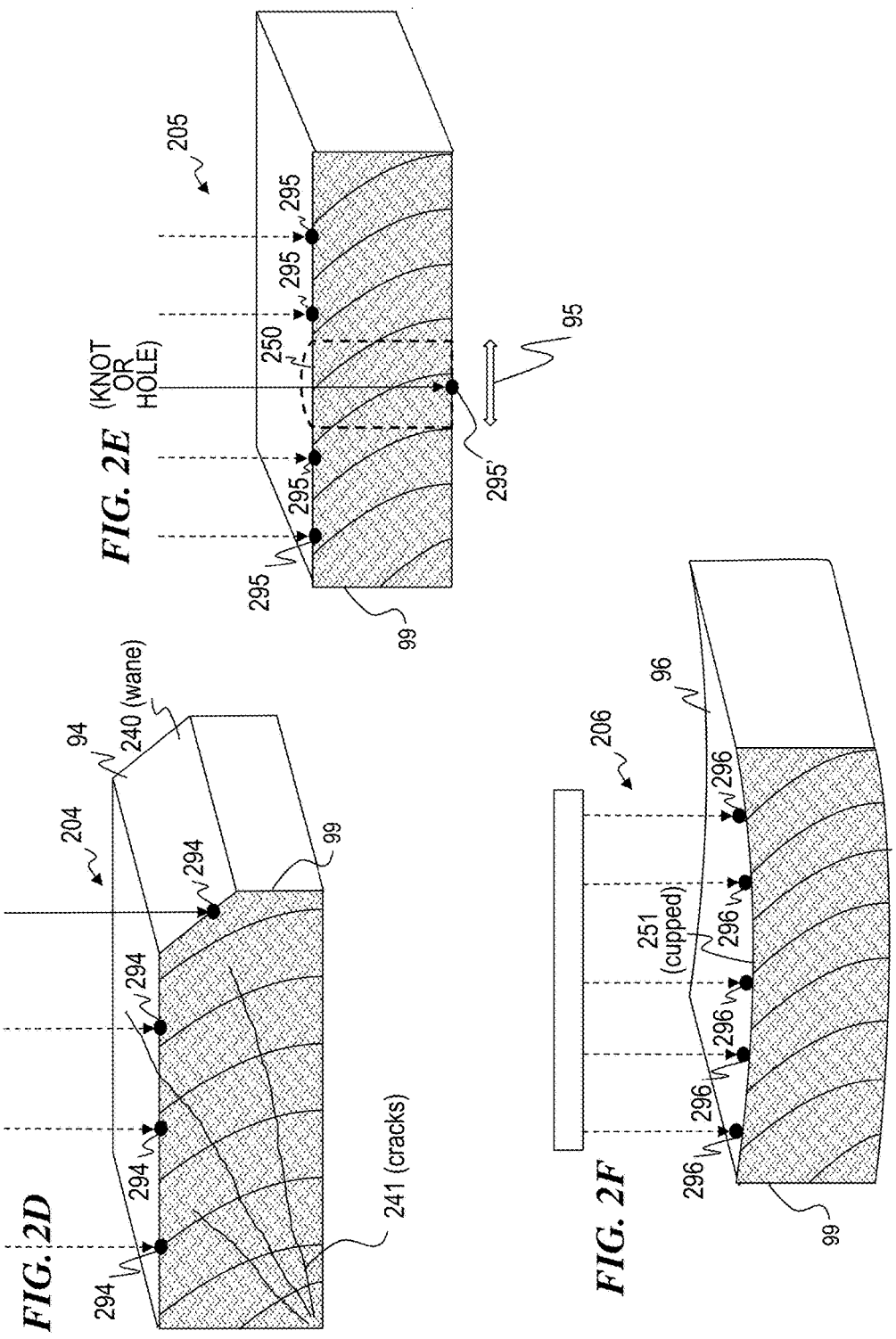

US 10,207,421 B1

AUTOMATED MULTI-HEADED SAW AND METHOD FOR LUMBER

CROSS-REFERENCE TO RELATED APPLICATION

This application claims priority benefit, under 35 U.S.C. § 119(e), of U.S. Provisional Patent Application 62/495,830, filed Sep. 26, 2016 by Steven Weinschenk, titled "MULTI-HEADED LINEAR SAW," which is incorporated herein by reference in its entirety. This invention is related to:

U.S. Provisional Patent Application 62/388,048, filed Jan. 14, 2016 by Steven Weinschenk, titled "AUTOMATED SYSTEM AND METHOD TO ENHANCE SAFETY AND STRENGTH OF WOOD TRUSS STRUCTURES,"

U.S. patent application Ser. No. 15/408,369, filed Jan. 14, 2017 by Steven Weinschenk, titled "AUTOMATED SYSTEM AND METHOD TO ENHANCE SAFETY AND STRENGTH OF WOOD TRUSS STRUCTURES,"

U.S. patent application Ser. No. 15/408,374, filed Jan. 14, 2017 by Steven Weinschenk, titled "AUTOMATED SYSTEM AND METHOD FOR LUMBER ANALYSIS,"

U.S. patent application Ser. No. 15/426,966, filed Feb. 7, 2017 by Steven Weinschenk, titled AUTOMATED SYSTEM AND METHOD FOR LUMBER PICKING,"

U.S. Provisional Patent Application 62/144,859 filed Apr. 8, 2015 by Steven Weinschenk, titled "DIGITAL PROJECTION SYSTEM AND METHOD FOR WORKPIECE ASSEMBLY"; and U.S. patent application Ser. No. 15/093,732 filed Apr. 7, 2016 by Steven R. Weinschenk et al., titled "DIGITAL PROJECTION SYSTEM AND METHOD FOR WORKPIECE ASSEMBLY";

which are each incorporated herein by reference in their entirety.

FIELD OF THE INVENTION

The present invention relates to devices and methods to workpiece assembly, and in particular to automated multi-headed saw systems and methods for lumber sawing that use two single-contact-point "fence posts" that are optionally associated with and move with each one of a plurality of saw heads in order to securely hold and support boards that may have curved sides (due to crooks or warps), rather than boards having straight sides aligned along a straight-wall conventional saw fence. Some embodiments organize each incoming stack of lumber in one of a plurality of vertically spaced apart bunks, one on top of another, and provide a gantry that picks a selected board from the stack of lumber on a selected bunk, and moves the board in a direction generally perpendicular to the long axis of the board from the selected bunk to one of possibly multiple copies of the multi-headed sawing station, thereby shortening the distance traveled between the bunks and the saws. Some embodiments further include a conveying mechanism that moves the cut boards to a truss-assembly table, where a product such as a truss or stud-wall section is finished.

BACKGROUND OF THE INVENTION

One problem with today's conventional technology is that, when manually loading wood into the infeed systems, the human operator needs to determine how to orient the wood, which increases the cost of labor when manufacturing structures using wood boards (lumber). As used herein, "crook" is a lumber feature or defect where the widest faces of the piece of lumber are substantially planar but there is a curvature along the length of the narrower faces of the piece of lumber. The "crown" is the convex one of the narrower faces of the piece of lumber with a crook. The crown should be orientated to optimize with the wood saw equipment. Certain wood trusses and pre-assembled walls are more secure if the crown of the wood is oriented correctly (both when the board is loaded into a sawing station, and when the cut board is assembled into a truss, a pre-assembled wall, or the like). Conventional automated or partially automated systems are unable to determine and/or distinguish the crown of the lumber.

U.S. Pat. No. 4,196,648 to Jones, et al. issued on Apr. 8, 1980 with the title "Automatic sawmill apparatus" and is incorporated herein by reference. U.S. Pat. No. 4,196,648 describes a cant or plank is moved forwardly on a conveyor system, where its irregular leading lateral edge is measured by a plurality of fixed scanners. In response to measurement of the cant, conveyor movement is altered for orienting the cant relative to a fixed saw line to be executed by a movable saw. The cant is held or clamped in stationary position while the saw is moved on a carriage relative thereto, resulting in severing of the undesired irregular forward edge. The sawn edge is employed as a reference as the cant is then moved forwardly on a conveyor system, where the measurements obtained from the scanners may be further utilized in cutting the cant into desired widths.

U.S. Pat. No. 4,909,112 issued to Rosenthal on Mar. 20, 1990 with the title "Multiple head gang saw with simplified, accurate displacement transducer," and is incorporated herein by reference. U.S. Pat. No. 4,909,112 describes a multiple head gang saw has a plurality of moveable saw heads providing variable width cutting, and a single magnetostrictive displacement transducer sensing displacement of all of the saw heads. The transducer sender unit is mounted to a transverse cross beam, and a magnetostrictive rod extends from the sender unit along and parallel to the cross beam. A plurality of pairs of electromagnets are mounted to respective saw heads proximate the magnetostrictive rod. Switching circuitry selectively energizes a chosen electromagnet pair and de-energizes the remaining electromagnet pairs such that only the chosen electromagnet pair generates a magnetic field interacting with the signal in the rod from the sender unit, such that the displacement transducer indicates the distance from the sender unit to the chosen electromagnet pair and its respective saw head along the cross beam.

United States Patent Publication 2005/0027389 by Hadaway et al. published on Feb. 3, 2005 with the title "Computer numerically controlled table saw fence" and is incorporated herein by reference. Publication 2005/0027389 describes a table saw control system. The system shortens the time required to learn how to operate a table saw, eliminates the necessity of making conversions from one measurement system or unit to another, reduces the likelihood of error occurring during the use of a table saw, and makes a table saw safer to use. The system includes a touch control screen mounted on the fence and moving simultaneously with the fence; and, a plurality of inter-related operational menus operatively associated with the computer and displayed sequentially on the screen and including button images activated by touch to generate signals to the computer to move from one of the menus to another of the menus and to control movement of the carriage and the fence.

U.S. Pat. No. 4,951,215 to Scherer issued on Aug. 21, 1990 with the title "Lineal output measurement circuit for use with product cutting apparatus" and is incorporated herein by reference. U.S. Pat. No. 4,951,215 describes a lineal output measurement circuit adapted for use with product cutting apparatus, primarily with wood cutting apparatus of the type which have a plurality of simultaneously operable cutting elements. This product cutting apparatus is thereby capable of cutting product stock, such as ripping of a wood member simultaneously into individual wood section strips with a plurality of saw blades positioned to cut the individual strips. The apparatus generally includes some form of input mechanism for programming the cutting mechanism to produce the individual sections of product, that is, to produce the desired amount of the selected widths of product. The measurement circuit of the present invention utilizes program electrical signals from the apparatus which provide a program input representative of the different sizes of product sections to be produced, along with a port circuit and a processing means. The processing means calculates the amount of product sections cut from the product stock and generates output signals therefor.

U.S. Pat. No. 8,010,216 to Roise issued on Aug. 30, 2011 with the title "System and method for cutting-stock optimization across schedules and batches" and is incorporated herein by reference. U.S. Pat. No. 8,010,216 describes a method and system for optimizing cutting of various materials. In some embodiments, an algorithm optimizes cutting by grouping items to be cut, wherein two or more of a plurality of cutting-stock pieces are grouped together and aligned such that a single cut simultaneously cuts items from all of the pieces. Some embodiments optimize a combination of reduced labor cost, reduced materials cost (e.g., reducing scrap), and/or reduced time needed to obtain an inventory of pieces cut to specified lengths and shapes (checking the various permutations). Overall optimization of labor and material is achieved by a combination of fewer cuts and reduced waste. Some embodiments include a computer-readable medium having instructions executed by a computer that optimizes placement of cuts to obtain cut-part items, and optionally controls a saw, laser, water-jet cutter or the like. In some embodiments, a human operator making the cuts is instructed by the computer to achieve the optimization.

U.S. Pat. No. 6,170,163 to Robert A. Bordignon et al. titled "METHOD OF ASSEMBLING COMPONENTS OF AN ASSEMBLY USING A LASER IMAGE SYSTEM," issued Jan. 9, 2001, and is incorporated herein by reference. In U.S. Pat. No. 6,170,163 Bordignon et al. describe a method of assembling components of an assembly, such as the components of a truss, using a laser imaging system in combination with assembly jigs. The jigs may be slideably mounted on an assembly table wherein the jigs include laser alignment indicia on a top surface of the jigs spaced a predetermined distance from a side surface of the jigs. The method includes projecting an enlarged laser generated outline of at least a portion of the components to be assembled which is spaced laterally from an outline or template of the components in the assembled position a distance equal to the distance between the laser alignment indicia and the side surface of the jigs and spaced vertically a distance equal to the distance between the indicia and the work surface. The jigs are then moved on the work surface to align the laser alignment indicia with the enlarged outline and affixed relative to the work surface. Finally, the components are assembled on the work surface in generally abutting relation with the side surfaces of the jigs and assembled. Where the assembly method of this invention is used for assembling trusses, the laser generated outline may be used to orient the truss planks.

U.S. Pat. No. 7,463,368 to Morden et al. titled "LASER PROJECTION SYSTEM, INTELLIGENT DATA CORRECTION SYSTEM AND METHOD" issued Dec. 9, 2008, and is incorporated herein by reference. In U.S. Pat. No. 7,463,368 Morden et al. describe a laser projection system, intelligent data correction system and method which corrects for differences between the as-built condition and the as-designed condition of a workpiece which includes determining the as-built condition of a workpiece with a digitizer scanner and modifying data of the as-built condition or the data of a laser projection based upon the data received from the digitizer scanner of the as-built condition. A preferred intelligent data correction system includes metrology receivers fixed relative to the digitizer scanner and the workpiece and a metrology transmitter to determine the precise location and orientation of the digitizer scanner relative to the workpiece.

U.S. Pat. No. 7,621,053 to Edward S. Bianchin titled "ASSEMBLY APPARATUS," issued Nov. 24, 2009, and is incorporated herein by reference. In U.S. Pat. No. 7,621,053 Bianchin describes an assembly apparatus for assembling components including a work surface, a laser projector, a computer controlling the laser projector to protect a laser image on the work surface, and an ejector lifting a completed assembly from the work surface having a retro-reflective surface within a field of view of the laser projector when the ejector is lifted, such that the laser projector scans the retro-reflective surface and the computer determines at least one of the number of completed assemblies made and the time required to make the assembly.

United States Patent Publication 2010/0201702 of Franik et al. published Aug. 12, 2010 with the title "DIGITAL IMAGE PROJECTION LUMINAIRE SYSTEMS," and is incorporated herein by reference. In Patent Publication 2010/0201702 Franik et al. describe improvements to digital imagine projection systems and for seamless blending of images projected from a plurality of digital image projectors to create combined images from multiple projectors where the user is provided with independent control of the blend area and of independent control of image parameters within said variable blend area such as brightness, contrast, individual color intensity and gamma correction.

U.S. Pat. No. 8,079,579 to Fredrickson et al. titled "Automatic truss jig setting system," issued Dec. 20, 2011, and is incorporated herein by reference. In U.S. Pat. No. 8,079,579 Fredrickson et al. describe an automatic truss jig setting system that includes a table including a plurality of segments with a side edge of adjacent segments defining a slot. At least one pin assembly, and optionally a pair of pin assemblies, is movable independently of each other along the slot. Movement apparatus is provided for independently moving the pin assemblies along the slot. Each of the side edges of the segments associated with the slot defines a substantially vertical plane with a zone being defined between the substantially vertical planes of the side edges, and the movement apparatus is located substantially outside of the zone of the slot. The invention may optionally include a system for handling the obstruction of pin assembly movement, and a system for keeping track of the position of the pin assembly when the pin assembly has encountered an obstruction.

U.S. Pat. No. 8,782,878 to Morden et al., titled "FASTENER AUTOMATION SYSTEM," issued Jul. 22, 2014, and is incorporated herein by reference. In U.S. Pat. No. 8,782,878, Morden et al. describe a fastener automation system for assembly of fasteners to a substrate, which includes a projection system for projecting an image on a substrate of a predetermined location of a correct fastener to be installed in the substrate and data relating to the correct fastener and the substrate, and a computer operably associated with the projection system storing data regarding the correct fastener and the predetermined location on the substrate where the correct fastener is to be installed. An automated method of installing a fastener in a substrate at a predetermined location includes using a projector system to identify a predetermined location for installation of a correct fastener to the substrate, collecting data regarding the correct fastener installation at the predetermined location and storing the data in a computer, and installing the correct fastener in the substrate at the predetermined location based upon the data.

United States Patent Publication 2008/0297740 of Huynh et al. published Dec. 4, 2008 with the title "Projection system and method of use thereof," and is incorporated herein by reference. In Patent Publication 2008/0297740 Huynh et al. describe a projection system and method of use thereof, wherein a computer in electrical communication with at least one projector projects a layout, preferably onto a floor projection surface utilizing short throw lenses, wherein the layout preferably comprises a grid and indicia relating to an exhibitor.

U.S. Pat. No. 8,919,001 to Le Mer et al. titled "METHOD AND SYSTEM FOR HELPING TO POSITION A COMPONENT ON A STRUCTURAL ELEMENT," issued Dec. 30, 2014, and is incorporated herein by reference. In U.S. Pat. No. 8,919,001 Le Mer et al. describe a method for helping to position a component on the wall of a structural element, including the steps: elaborating an image to be projected on the wall, from a virtual model of the structure and from the positioning of a projector with respect to the structure, and an additional motif providing positioning information of the piece with respect to the direction normal to the wall, projecting the image on the structural element by means of the projector; placing the base of the piece inside an outline of the image projected on the wall; and, while keeping contact between the piece and the structural element, modifying the positioning of the piece with respect to the direction normal to the wall, until the predefined set of points of the piece coincides with the motif.

U.S. Pat. No. 8,960,244 to Aylsworth et al. titled "AUTOMATED LUMBER RETRIEVAL AND DELIVERY," issued Feb. 24, 2015, and is incorporated herein by reference. In U.S. Pat. No. 8,960,244 Aylsworth et al. describe an automated lumber handling system that laser-scans the top profile of multiple stacks of lumber, each of which contain boards of a unique size. Based on the scanned profiles, the system determines the order in which individual boards from a chosen stack should be transferred to a numerically controlled saw. The saw cuts the boards to proper size, and in the proper sequence to facilitate orderly assembly of a roof truss or prefabricated wall. In some examples, the system lifts individual boards by driving two retractable screws, or some other piercing tool, down into the upward facing surface of the board. A track mounted cantilever, holding the screws and a laser unit, translates over the lumber stacks to retrieve and deliver individual boards and, while doing so, the laser repeatedly scans the stacked lumber profiles on-the-fly to continuously update the profiles. The open cantilever design facilitates replenishing the stacks of lumber.

Chinese Patent Publication CN 202899636 U published Apr. 24, 2013 with the title "Discrete assembly device for large-span rectangular spatially warped tube truss," and is incorporated herein by reference. This Chinese Patent Publication CN 202899636 describes a discrete assembly device for a large-span rectangular spatially warped tube truss. The device consists of a base, two supporting tubes fixedly connected to the two sides of the base, and tube brackets fixedly connected to the tops of the supporting tubes, wherein grooves of which the diameter is matched with that of a lower chord of an assembly section truss are formed on the tube brackets. The on-site assembly difficulty of the large-span rectangular spatially warped truss is reduced, assembly accuracy and speed are greatly improved, and construction materials are saved.

There is a need in the art for better sawing stations and for systems cut two or more boards having various lengths and end-angles from a single piece of stock lumber that may be warped, twisted, and/or crooked, wherein the system shortens the path along which a piece of lumber moves, while performing lumber analysis, sorting, adjustment, and sawing of boards for assembly of a product, such as the assembly of wooden roof trusses, pre-assembled walls, and the like.

SUMMARY OF THE INVENTION

In some embodiments, the present invention provides a multi-headed sawing station that supports a piece of lumber on a substantially horizontal support bar located at each one of two saw heads, wherein the piece of lumber is also held against two single-point-of-contact substantially vertical fence posts, one associated with each one of the saw heads. In some embodiments, both saw heads move downward simultaneously to simultaneously cut two desired boards from the ends of the piece of lumber. In some embodiments, each saw head then automatically moves toward a center of the piece of lumber, while the board is supported by the horizontal support bar located at each saw head, and the board is also held to prevent slipping as the horizontal support bars move towards one another. In some embodiments, both saw heads again move downward simultaneously to simultaneously cut two more desired boards from the ends of the piece of lumber. In some embodiments, each saw head is independently rotatable around a vertical axis, in order that the ends of the desired cut boards are at a desired angle as well as at a desired length. In some embodiments, each saw head is also independently rotatable around a horizontal axis, in order that the ends of the desired cut boards are at a desired compound angle as well (i.e., angled at both a horizontal angle and a vertical angle).

In some embodiments, the present invention also provides a vacuum-activated picker arm that includes a plurality of suction cups that are optionally staggered at one or more distances on either side of a straight line, in order that if one or more of the suction cups fails to achieve a satisfactory grip on a piece of lumber (perhaps due to a crack or other defect in the piece of lumber, others of the plurality of suction cups will achieve enough of a grip to reliably pick up and move the piece of lumber. Some embodiments further include a plurality of compressed-air blowers to remove sawdust or other debris that may be on the piece of lumber, in order to reduce the amount of leakage at the plurality of suction cups. Some embodiments further include a plurality of compressed-air blowers to speed the release of the piece of lumber once it reaches its destination.

In some embodiments, the present invention provides a method and associated system that includes a computer processor, wherein the computer processor includes: a plurality of input data devices, a plurality of output data devices, and a plurality of sensors, and wherein the system further includes a mechanical assembly integrated with the computer processor to analyze the geometry of a piece of wood or lumber and, if necessary, reposition the piece and convey the piece to a saw or to a reject station, based on software code executing in the computer processor. Some embodiments organize each incoming stack of lumber in one of a plurality of vertically spaced apart bunks, one on top of another, and provide a gantry that picks a selected board from the stack of lumber on a selected bunk, and moves to board in a direction generally parallel to the long axis of the board from the bunk to one of a plurality of processing stations, wherein the plurality of processing stations includes a flipping station and/or a sawing station. Organizing the lumber bunks in vertical assemblies greatly reduces the footprint of the overall system, thus making more efficient use of valuable factory space and reducing costs. Using the present invention, one can buy lower-grade lumber and sort the boards to obtain suitable and usable pieces for a given end product, thus reducing cost and improving quality of the end product.

In some embodiments, the present invention provides a system and associated method that operates on a computer processor having a plurality of input data devices, a plurality of output data devices, a plurality of sensors, a database, software code, and a wireless interface, wherein the computer processor is integrated with mechanical components, and wherein the method includes eliciting and receiving into the computer processor data parameters from a first human user; obtaining incoming data points about lumber from the plurality of sensors (e.g., in some embodiments, from optical point distance sensors and/or three-dimensional (3D) machine-vision systems); processing the data parameters to obtain processed data parameters; storing the processed data parameters; comparing the incoming data points from the plurality of sensors to the stored data parameters to obtain comparison results; and, based on the comparison results, (1) directing the mechanical components to reject the wood to a preprogrammed position, (2) directing the mechanical components to feed the lumber into a saw assembly as positioned, or (3) directing the mechanical components to reposition the lumber to a more optimal position prior to feeding the lumber to a saw assembly.

BRIEF DESCRIPTION OF THE FIGURES

FIG. 1B is a schematic top-view diagram of a saw head 110 that can move left-to-right to one of several positions, and that can rotate around a vertical axis in order to accurately cut a plurality of relatively short boards having different horizontal cut angles from a piece of lumber 99, according to some embodiments of the present invention.

FIG. 1C is a schematic side-perspective-view diagram of a saw head 110 that can move left-to-right and can rotate around a vertical axis (and, in some embodiments, also around a horizontal axis) in order to accurately cut a plurality of relatively short boards having different horizontal- or compound-cut angles from a piece of lumber 99, according to some embodiments of the present invention.

FIG. 1D is a schematic front-perspective-view diagram of a saw head 110 (e.g., which could be used for 110A and/or 110B) that can move left-to-right and can rotate around a vertical axis in order to accurately cut a plurality of relatively short boards having different horizontal cut angles from a piece of lumber 99, according to some embodiments of the present invention.

FIG. 1E is a schematic front-perspective-view diagram of portions of saw system 101 that has a plurality of heads 110 (e.g., 110A and 110B in this figure) that each can move left-to-right and can rotate around a vertical axis and/or a horizontal axis in order to accurately cut a plurality of relatively short boards having different horizontal- or compound-cut angles from a piece of lumber 99, according to some embodiments of the present invention.

FIG. 2D is a schematic diagram 204 showing exemplary data points used to detect wane 240 and cracks 241 in a piece of lumber 99, according to some embodiments of the present invention.

FIG. 2E is a schematic diagram 205 showing exemplary data points used to detect a knot 250 in a piece of lumber 99, according to some embodiments of the present invention.

FIG. 2F is a schematic diagram 206 showing exemplary data points used to detect cupping 251 in a piece of lumber 99, according to some embodiments of the present invention.

COPYRIGHT NOTICE/PERMISSION

Figure 1A:
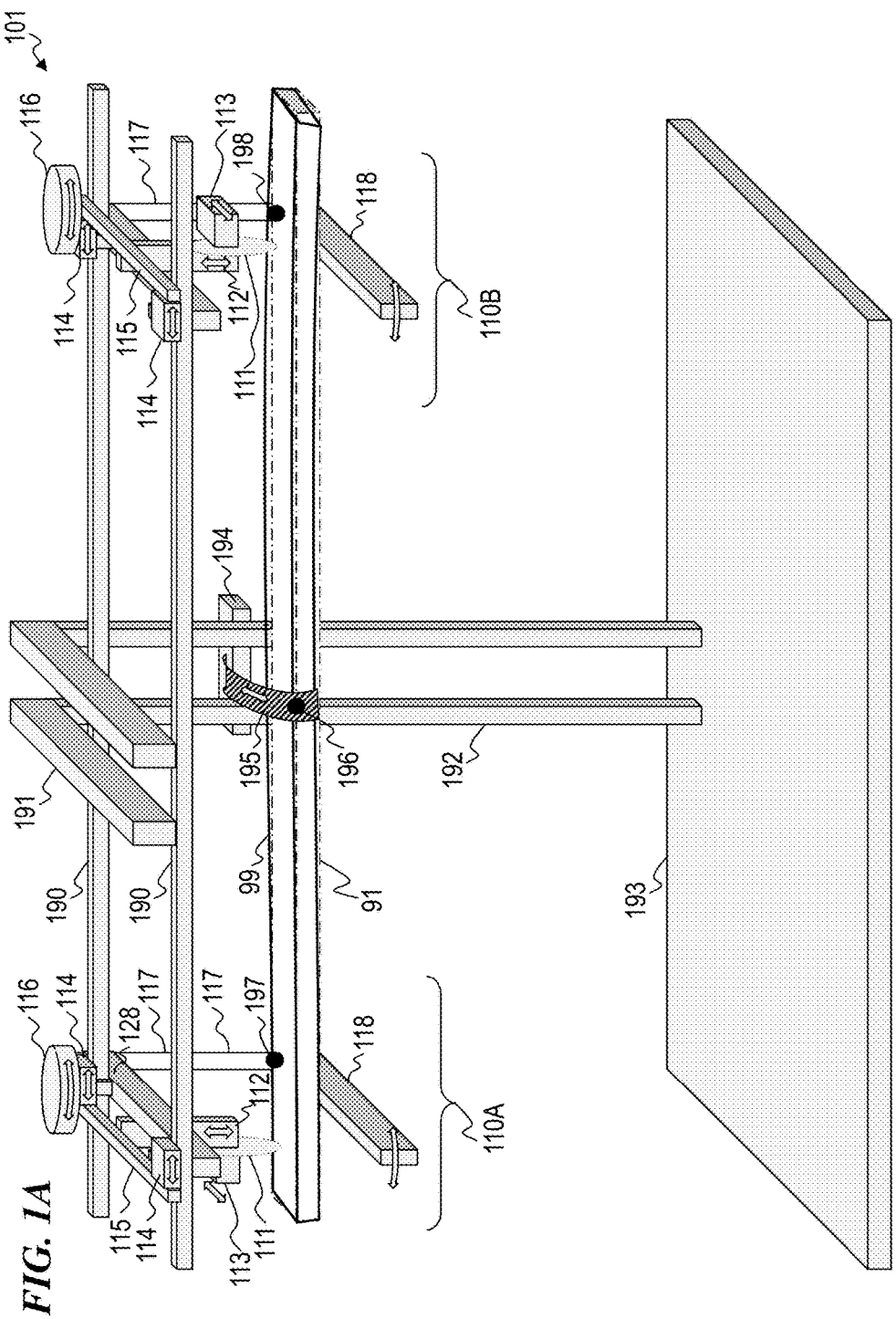
FIG. 1A is a schematic front-perspective-view diagram of a saw system 101 that has a plurality of heads 110 (e.g., 110A and 110B in this figure) that can move left-to-right and can rotate around a vertical axis in order to accurately cut a plurality of relatively short boards having different horizontal cut angles from a piece of lumber 99, according to some embodiments of the present invention.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described herein and in the drawings hereto in the attached appendices: Copyright© 2014-2017, Steven R. Weinschenk, All Rights Reserved.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

As used herein, "crook" is a lumber feature or defect where the widest faces of the piece of lumber are substantially planar but there is a curvature along the length of the narrower faces of the piece of lumber. The "crown" is the convex one of the narrower faces of the piece of lumber with a crook. See FIG. 2A.

As used herein, "bow" is a lumber feature or defect where the narrower faces of the piece of lumber are substantially planar but there is a curvature along the length of the wider faces of the piece of lumber. See FIG. 2B.

As used herein, "twist" is a lumber feature or defect in which there are curvatures across multiple surfaces in the lumber. See FIG. 2C.

As used herein, "wane" is a lumber feature or defect that is characterized by bark or insufficient wood at a corner or along an edge, due to the piece of lumber being cut from an outer edge of the log. See FIG. 2D.

As used herein, "knot" is a lumber feature or defect that is characterized by a separated branch piece or hole in a piece of lumber. See FIG. 2E.

As used herein, "cup" is a lumber feature or defect where there is a curvature across the width of the widest face of the lumber, in which the edges are higher or lower than the center of the piece of lumber. See FIG. 2F.

FIG. 1A is a schematic front-perspective-view diagram of a saw system 101 that has a plurality of saw-head assemblies 110 (e.g., 110A and 110B in this figure) that can move left-to-right and can rotate around a vertical axis in order to accurately cut a plurality of relatively short boards having different horizontal cut angles from a piece of lumber 99, according to some embodiments of the present invention. In some embodiments, saw system 101 includes a support stand 191-192 that extend upward from base 193. In some embodiments, the support stand 192, 192, 193 holds one or more horizontal support rails 190 upon which the plurality of saw heads 110 move. In some embodiments, a grip actuator 194 is configured to move gripper arm 195 to press against board 99 at location 196 to urge board 99 downward against board-support arms 118 of each saw head 110A and 110B, and inward against locations 197 and 198. In some embodiments, gripper arm 195 reaches over board 99, lowers its curved (e.g., hook-shaped) distal end around board 99 and then pulls board 99 down and in against fence-post rod 117 support rod 118 of both saw-head assemblies 110A and 110B. In some embodiments, gripper arm 195 includes two jaws that clamp two opposite faces (top and bottom or far and near sides) of board 99. In some embodiments, a plurality of grip actuators 194 and gripper arms 195 are provided (e.g., in some embodiments, one set of gripper arm-actuators on each saw-head assembly 110A and 110B). In some embodiments, board-support arms 118 and/or "fence post" rods 117 are each cylindrical (e.g., see FIG. 1B) in order to provide stable contact points and minimize possible rocking motion of warped or twisted boards. In other embodiments, board-support arms 118 and/or "fence post" rods 117 are each rectangular, triangular or other suitable shapes as needed to suit the requirements of boards having possible board defects (i.e., boards that are not perfectly straight and rectangular). The substantially three-point contact arrangement 196-197-198 accommodates twisted or warped or crooked boards while minimizing the rocking that commonly occurs when holding a convexly curved board against a conventional straight-wall saw fence. This allows more accurate cuts and can improve safety by not having the workpiece shift part-way through a cut (which can cause a piece of board to fly out at high speed). The dash-dot outline 91 represents a hypothetical straight board that is otherwise similar to actual board 99, which is shown in solid lines. In some embodiments, each saw-head assembly 110A and 110B includes a saw blade 111 that is rotated by motor 113 (and/or moved in a direction parallel to a line above board-support beam 118 toward and away from "fence post" rod 117 by a linear actuator coupled to and associated with motor 113), which is raised and lowered by up-down actuator 112, that is attached to support beam 115. In some embodiments, support beam 115 is attached to two linear actuators 114 that move the respective saw-head assembly 110A and 110B leftward and rightward along the one or more horizontal support rails 190. In some embodiments, rotation actuator 116 rotates cylindrical "fence post" rod 117, which holds bottom board-support arm 118 and upper support arm 128, around its longitudinal axis (which is substantially vertical in this embodiment). Being cylindrical, rod 117 provides a single back support point 197 or 198 against which board 99 rests regardless of the amount of angular rotation actuator 116 provides around the vertical rotation axis. In some embodiments, board-support arm 118 is also cylindrical so that rotation around a horizontal axis also presents a constant vertical distance of the board from the horizontal longitudinal axis of board-support arm 118. In some embodiments, board support arm 118 and upper support arm 128 are cantilevered from "fence post" rod 117 near its lower and upper ends, respectively. In some embodiments, upper support arm 128 provides an anchor position for up-down actuator 112 which is connected to motor 113, such that when angular rotation actuator 116 rotates "fence post" rod 117, the entire saw portion 111, 112, 113, 118 and 128 all rotate together to the same angle as "fence post" rod 117, such that saw blade 111 always cuts off the severed end of board 99 right next to, and parallel to, board support arm 118. This provides excellent height control of the butt end of angled principal rafters of roof trusses, even when the source board 99 is somewhat crooked, twisted or warped. Thus, the present invention provides cut boards that have the correct desired lengths and cut angles (which are particularly important for even though the middle of the board is warped.

FIG. 1B is a schematic top-view diagram of a saw head 110 (shown here in three different positions and orientations) that can move left-to-right to one of several positions, and that can rotate around a vertical axis in order to accurately cut a plurality of relatively short boards having different horizontal cut angles from a piece of lumber 99, according to some embodiments of the present invention. FIG. 1B shows the same saw head 110 in three different horizontally displaced positions along top rails 190. In some embodiments, horizontal linear actuators 114 are used to move saw head 110 to the desired horizontally displaced position, while rotary actuator 116 is used to rotate saw head 110 to the desired angle relative to the longitudinal axis of board 99 (e.g., to cut the ends of primary rafters to the desired angle).

FIG. 1C is a schematic side-perspective-view diagram of a saw head 110 that moves left-to-right (using linear actuators 114), that rotates around a vertical axis (using rotary actuator 116), and, in some embodiments, that also rotates around a horizontal axis (using rotary actuator 136) in order to accurately cut a plurality of relatively short boards having different horizontal- or compound-cut angles from a source piece of lumber 99, according to some embodiments of the present invention. Due to the entire saw portion 111, 112, 113, 118 and 128 of saw head 110 all rotating together to the same angle as "fence post" rod 117

FIG. 1D is a schematic front-perspective-view diagram of a saw head 110 (e.g., which could be used for 110A and/or 110B) that can move left-to-right and can rotate around a vertical axis in order to accurately cut a plurality of relatively short boards having different horizontal cut angles from a piece of lumber 99, according to some embodiments of the present invention.

FIG. 1E is a schematic front-perspective-view diagram of portions of saw system 101 that has a plurality of heads 110 (e.g., 110A and 110B in this FIG. 1E) that each can move left-to-right (using linear actuators 114 to change the length of the board being cut) and can rotate around a vertical axis (using rotary actuator 116 to change the horizontal angle of the board being cut) and/or a horizontal axis (using rotary actuator 136 to change the vertical angle of the board being cut) in order to accurately cut a plurality of relatively short boards having different horizontal-angle (such as saw head 110A shown here cutting at a non-perpendicular horizontal angle relative to the length of board 99), vertical-angle (such as saw head 110B shown here cutting at a non-perpendicular vertical angle relative to the length of board 99) or compound-cut angles from a piece of lumber 99 (i.e., such as a saw head 110A or 110B cutting at both a non-perpendicular vertical angle and non-perpendicular horizontal angle relative to the length of board 99, not shown here but obvious to one of skill in the art, wherein both rotary actuator 116 and rotary actuator 136 rotate to set the saw blade to cut a compound-angle cut), according to some embodiments of the present invention.

Figure 1F:
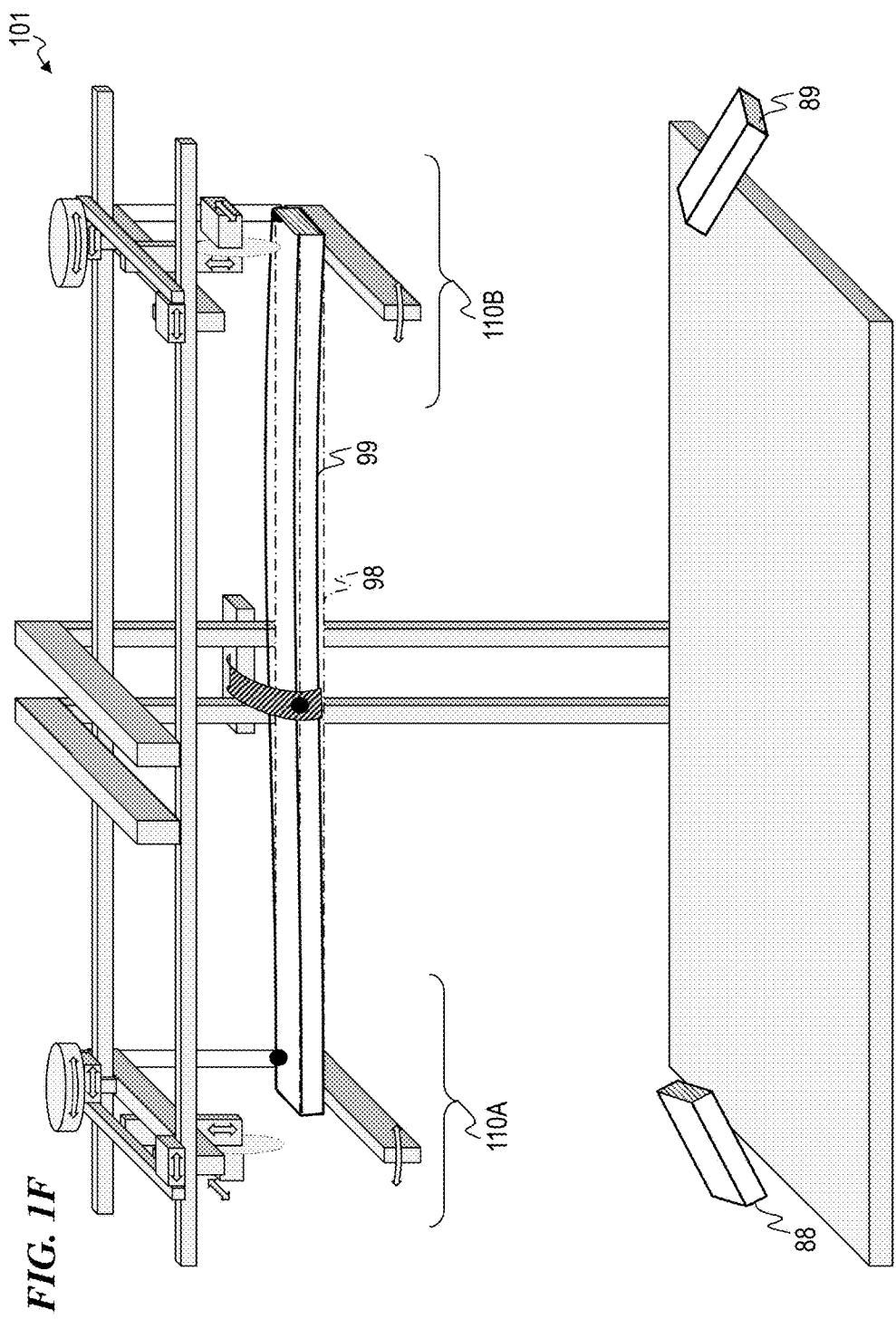
FIG. 1F is a schematic front-perspective-view diagram of saw system 101 of FIG. 1A a short time after that shown in FIG. 1A, i.e., just after two boards have been cut from piece of lumber 99, according to some embodiments of the present invention.

FIG. 1F is a schematic front-perspective-view diagram of saw system 101 of FIG. 1A a short time after that shown in FIG. 1A, i.e., just after two boards, 88 and 89, each having an end cut perpendicular to their long axes, have been cut from piece of lumber 99, according to some embodiments of the present invention.

Figure 1G:
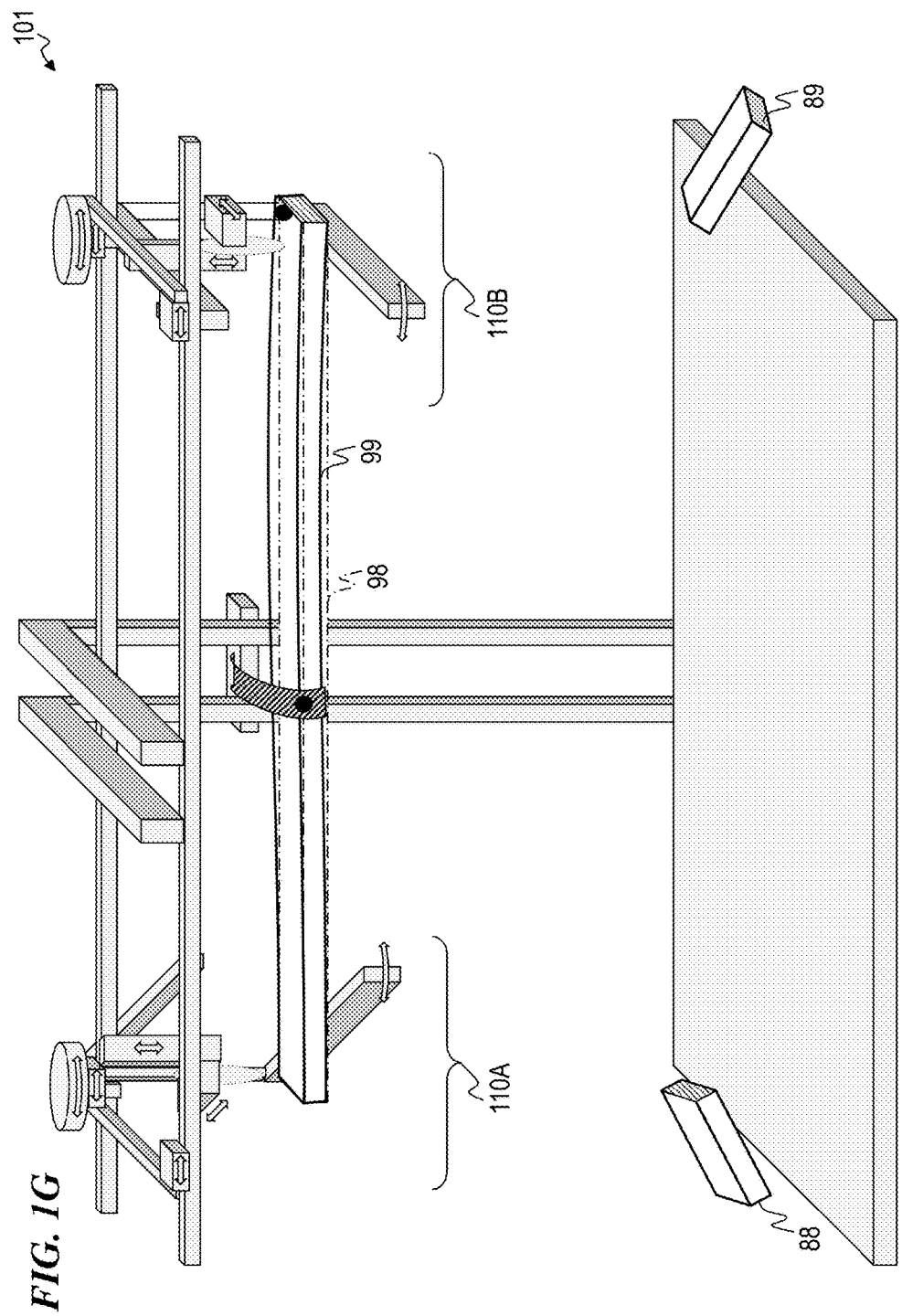
FIG. 1G is a schematic front-perspective-view diagram of saw system 101 of FIG. 1F a short time after that shown in FIG. 1F, i.e., just after rotating head 110A for the next cut, according to some embodiments of the present invention.

FIG. 1G is a schematic front-perspective-view diagram of saw system 101 of FIG. 1F a short time after that shown in FIG. 1F, i.e., just after rotating head 110A for the next angled cut, according to some embodiments of the present invention.

Figure 1H:
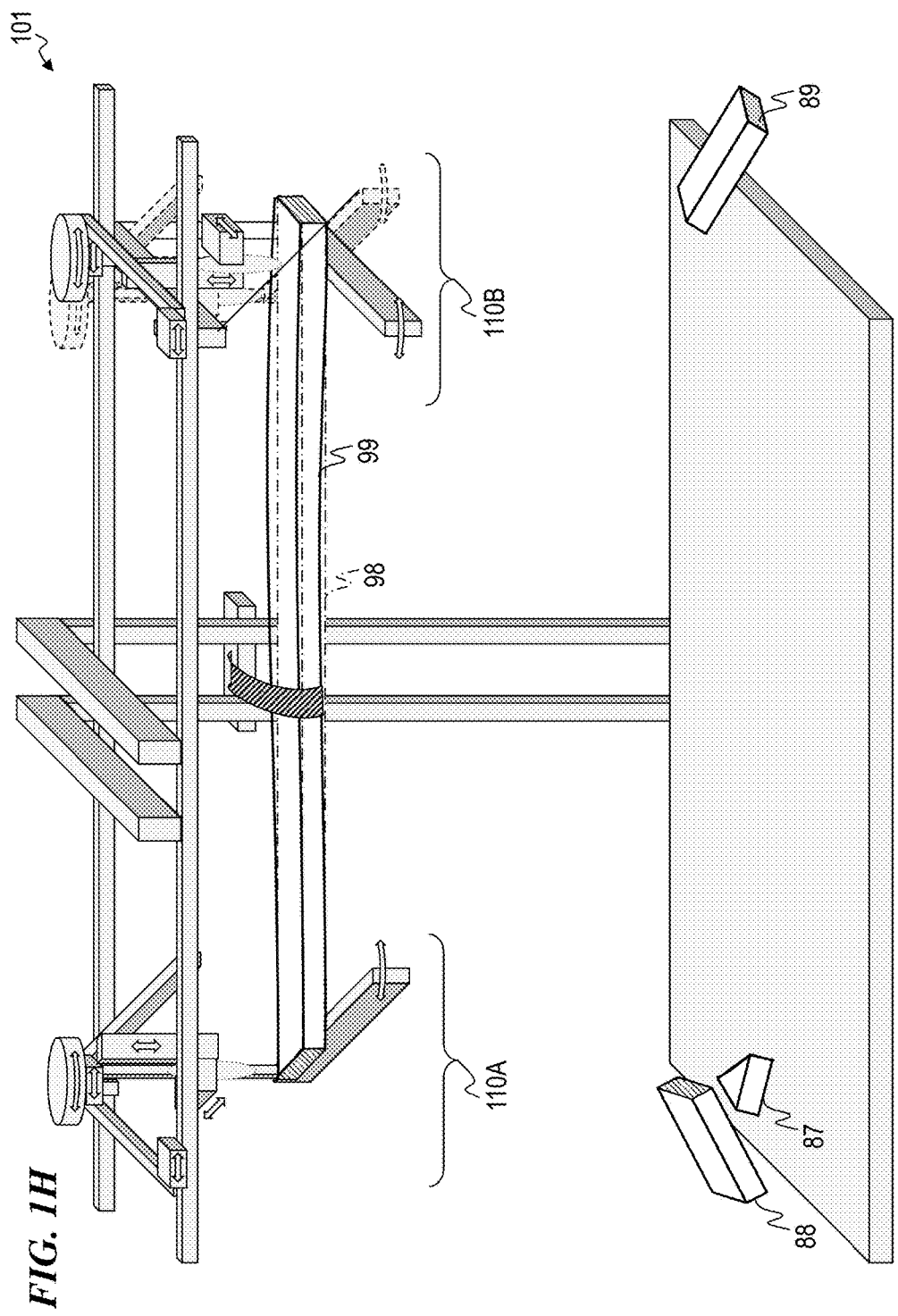
FIG. 1H is a schematic front-perspective-view diagram of saw system 101 of FIG. 1G a short time after that shown in FIG. 1G, i.e., just after cutting an angled piece using rotated head 110A, and possibly moving head 110B for the next cut, according to some embodiments of the present invention.

FIG. 1H is a schematic front-perspective-view diagram of saw system 101 of FIG. 1G a short time after that shown in FIG. 1G, i.e., just after cutting an angled piece 87 using rotated head 110A, and possibly moving head 110B for the next cut, according to some embodiments of the present invention.

Figure 1I:
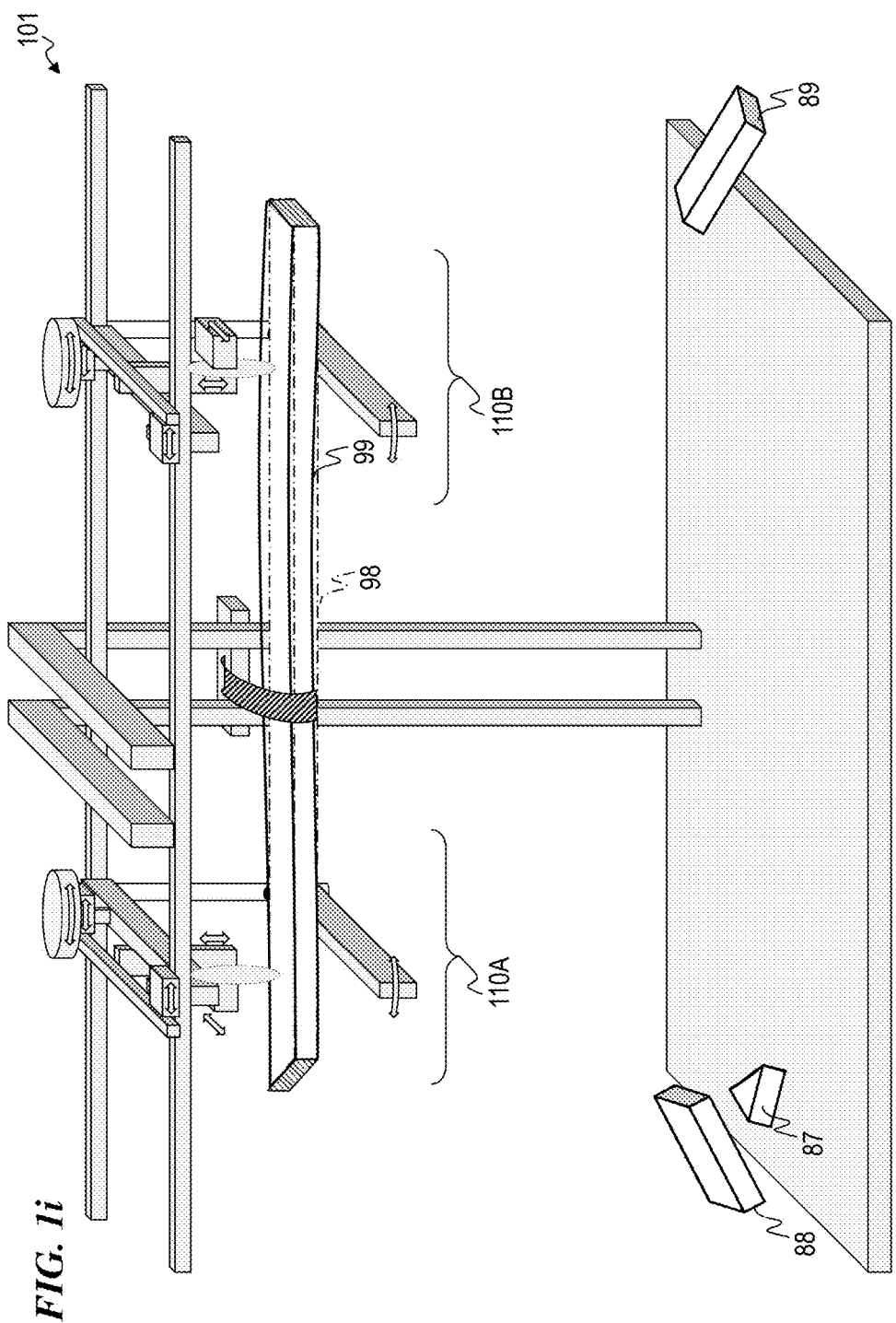
FIG. 1*i* is a schematic front-perspective-view diagram of saw system 101 of FIG. 1H a short time after that shown in FIG. 1H, i.e., just after moving head 110A and head 110B for the next cut, according to some embodiments of the present invention.

FIG. 1i is a schematic front-perspective-view diagram of saw system 101 of FIG. 1H a short time after that shown in FIG. 1H, i.e., just after moving head 110A and head 110B for the next two cuts, according to some embodiments of the present invention.

Figure 1J:
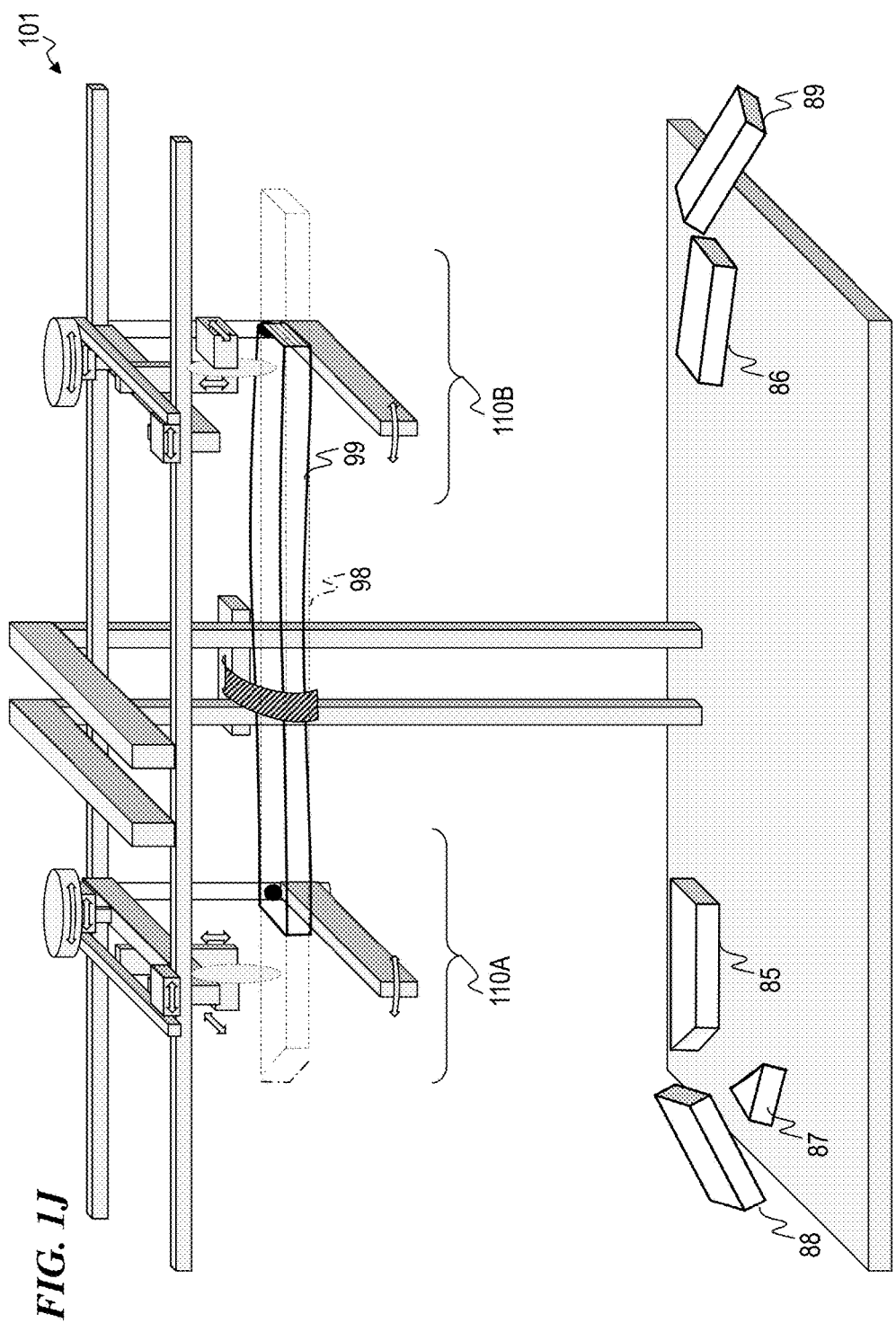
FIG. 1J is a schematic front-perspective-view diagram of saw system 101 of FIG. 1*i* a short time after that shown in FIG. 1*i*, i.e., just after two more boards have been cut from piece of lumber 99, according to some embodiments of the present invention.

FIG. 1J is a schematic front-perspective-view diagram of saw system 101 of FIG. 1i a short time after that shown in FIG. 1i, i.e., just after two more boards, 85, having an angled end cut, and 86, having an end cut perpendicular to its long axes, have been cut from piece of lumber 99, according to some embodiments of the present invention.

Figure 2A:
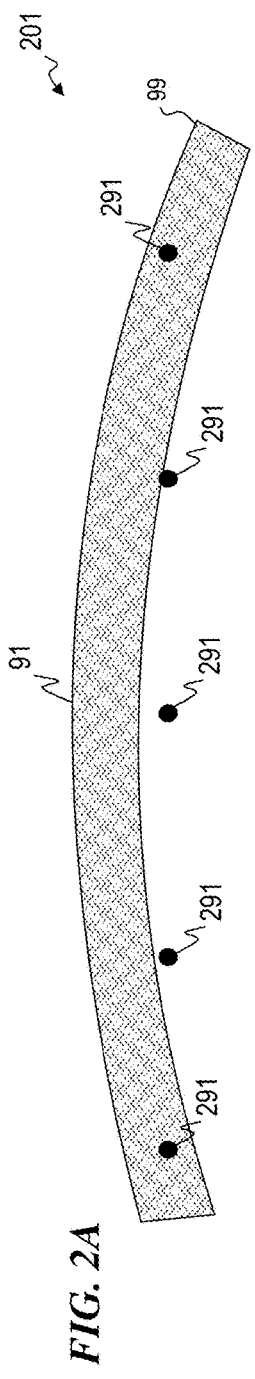
FIG. 2A is a schematic diagram 201 showing exemplary data points used to detect crook in a piece of lumber 99, according to some embodiments of the present invention.

FIG. 2A is a schematic diagram 201 showing a top view of a plurality of exemplary data points 291 that, in some embodiments, are gathered along the length of a board and used to detect crook in a piece of lumber 99, and if crook is detected, used to determine the crown face 91 and the amount of curve on the crown face 91, according to some embodiments of the present invention.

Figure 2B:
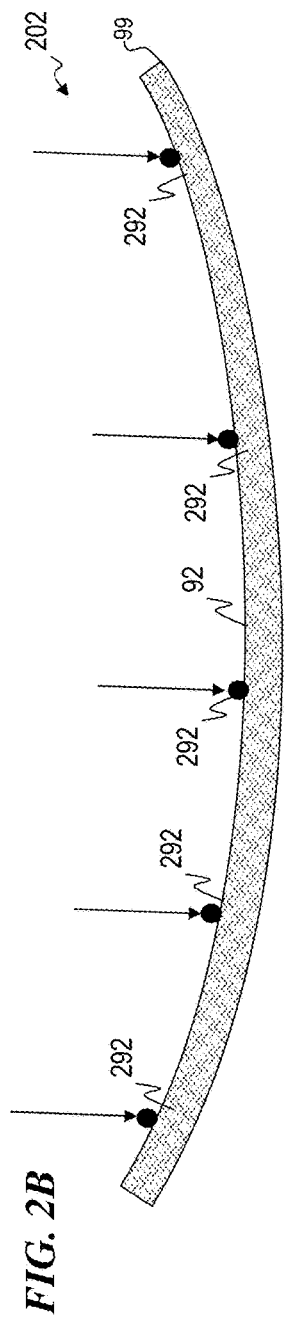
FIG. 2B is a schematic diagram 202 showing exemplary data points used to detect bow in a piece of lumber 99, according to some embodiments of the present invention.

FIG. 2B is a schematic diagram 202 showing a side view of a plurality of exemplary data points 292 that, in some embodiments, are gathered along the length of a board and used to detect bow in a piece of lumber 99, and if bow is detected, used to determine the amount and direction of curve on the bowed face 92, according to some embodiments of the present invention.

Figure 2C:
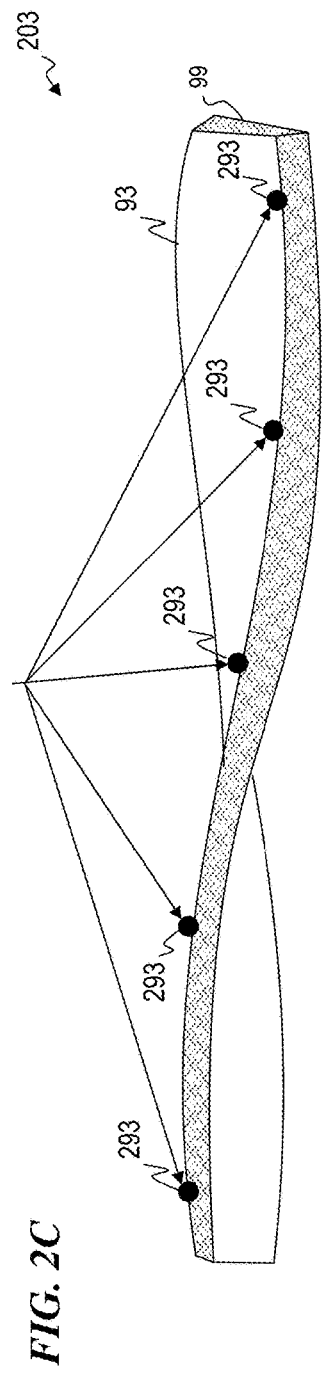
FIG. 2C is a schematic diagram 203 showing exemplary data points used to detect twist in a piece of lumber 99, according to some embodiments of the present invention.

FIG. 2C is a schematic diagram 203 showing a side view of a plurality of exemplary data points 293 that, in some embodiments, are gathered along the length of a board and used to detect twist in a piece of lumber 99, and if twist is detected, used to determine the amount and direction of curve on the twisted face 93, according to some embodiments of the present invention.

FIG. 2D is a schematic diagram 204 showing a perspective view of a plurality of exemplary data points 294 that, in some embodiments, are gathered across the width of a board and used to detect cracks 241 and wane 240 in a piece of lumber 99, and if cracks and/or wane are detected, used to determine the amount and position of any crack(s) and/or the amount and which corner(s) are missing on the wane surface 94, according to some embodiments of the present invention.

FIG. 2E is a schematic diagram 205 showing a perspective view of a plurality of exemplary data points 295 that, in some embodiments, are gathered across the width of a board and used to detect a knot 250 in a piece of lumber 99, and if one or more knots are detected, used to determine the size and position of any knots and/or the amount (size) and positions of the missing wood at the knot position 95, according to some embodiments of the present invention. In some embodiments, one or more of the data points (e.g., point 295') indicates a data point in the middle of a board that is well below the other data points 295 on the top surface.

FIG. 2F is a schematic diagram 206 showing a perspective view of a plurality of exemplary data points 296 that, in some embodiments, are gathered across the width of a board and used to detect cupping 251 in a piece of lumber 99, and if cupping is detected, used to determine the amount and direction of curve/cupping on the cupped face 96, according to some embodiments of the present invention.

Figure 3A:
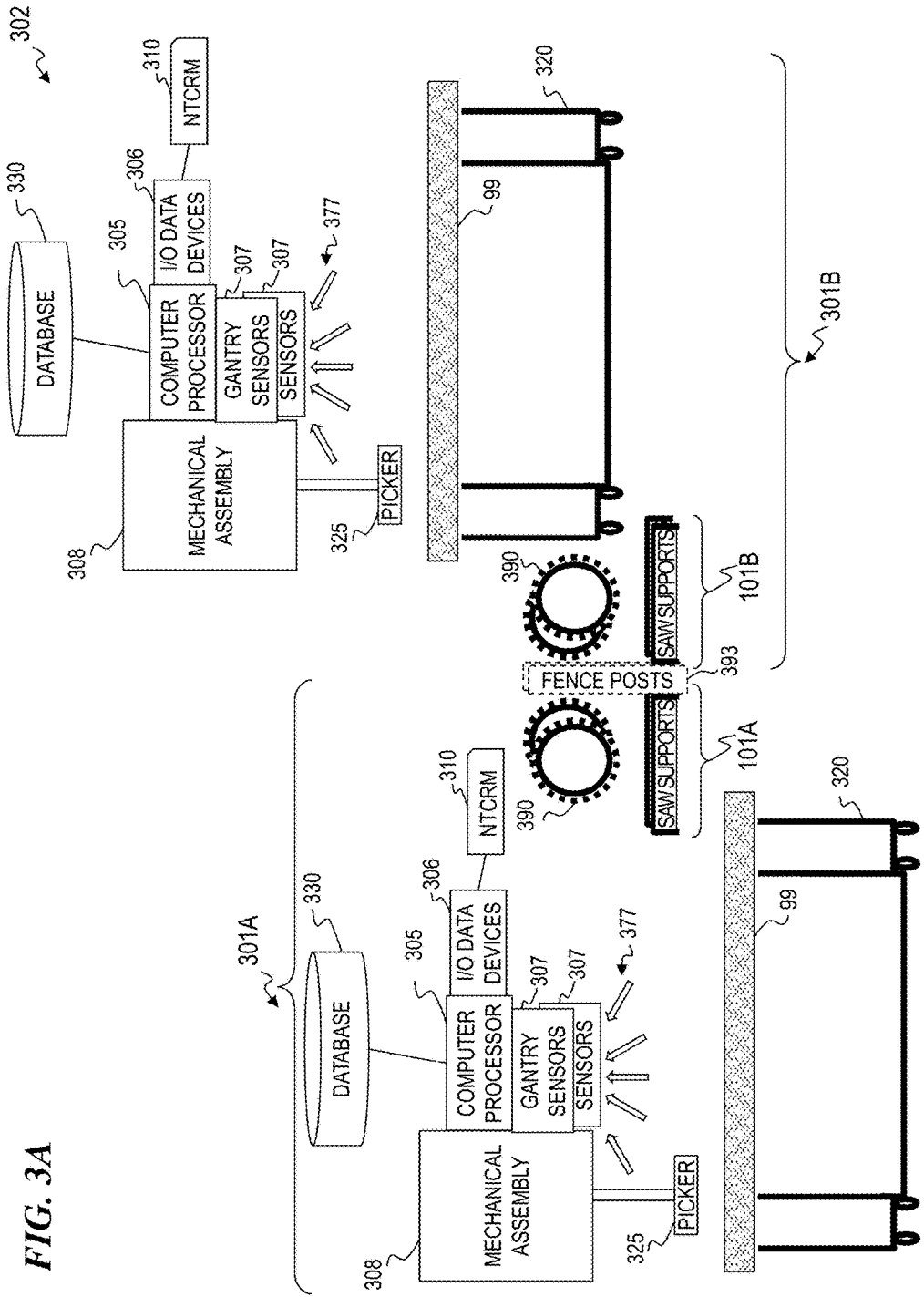
FIG. 3A is a side-view schematic diagram of a multi-station lumber-cutting system 302 that includes a plurality of lumber-transfer-and-cutting systems 301A, 301B, according to some embodiments of the present invention.

FIG. 3A is a side-view schematic diagram of a multi-station lumber-cutting system 302 that includes a plurality of dual-saw lumber-picking-and-cutting systems 301A, 301B, according to some embodiments of the present invention. In some embodiments, system 302 includes one or more saw systems 101 (e.g., in some embodiments, saw system 101A and saw system 101B; each embodying a saw system 101 as shown in FIG. 1A). In some embodiments, system 302 includes one or more computer processors 305 (in some embodiments, a Raspberry Pi® is used for processor 305 and is located on mechanical-assembly gantry 308, and uses open-source software (e.g., such as OPENCV) that has box, line, and color detection as well as knot and crack detection, where sometimes wane shows better in in images from a visual sensor due to the color of bark), wherein computer processor 305 includes a plurality of input/output data devices 306 and a plurality of gantry sensors 307 that obtain image, angle and/or distance data 377 from the top and/or side of one or more pieces of lumber 99 on cart 320, and/or bottom-side sensors (not shown here) that obtain image and/or distance data from the bottom of a piece of lumber 99 that has been removed from a cart 320 (e.g., in some embodiments, one of a plurality of such carts 320) as the piece of lumber is being moved toward the optional rejection station sensors (not shown here), the optional flip station sensors (not shown here) and/or one or more saw stations 390 (in some embodiments, each embodying a saw system 101; also see FIG. 3B). In some embodiments, each dual-saw lumber-picking-and-cutting systems 301A, 301B of system 302 further includes a mechanical assembly 308 on a gantry and integrated with computer processor 305 to grab (using picker assembly 325; e.g., such as described in co-pending U.S. patent application Ser. No. 15/426,966, filed Feb. 7, 2016, titled AUTOMATED SYSTEM AND METHOD FOR LUMBER PICKING," which is incorporated herein by reference) and reposition a piece of wood lumber 99 based on software code executing in computer processor 305 that processes the point location data received from gantry sensors 307 and/or bottom-side sensors 307'. In some embodiments, a database 330 (containing criteria-and-action data for each one of a plurality of end products to be made from the lumber) is operatively coupled to computer processor 305. In some embodiments, a non-transitory computer-readable medium 310 (storing thereon instructions for performing the method of the present invention) is connectable to computer processor 305, for example, via one or more of the plurality of input/output data devices 306. While multi-station lumber-cutting system 302 is shown as including duplicate versions of certain units (such as database 340), other embodiments share single copies of various units among the plurality of dual-saw lumber-picking-and-cutting systems 301A, 301B shown here. Some embodiments use a single dual-saw lumber-picking-and-cutting system 301A, while other embodiments use more than two. Other embodiments use a single set of one or more carts 320 that are centrally located and position the saw systems 101A and 101B on opposite sides of the centrally located set of cart(s) 320.

Figure 3B:
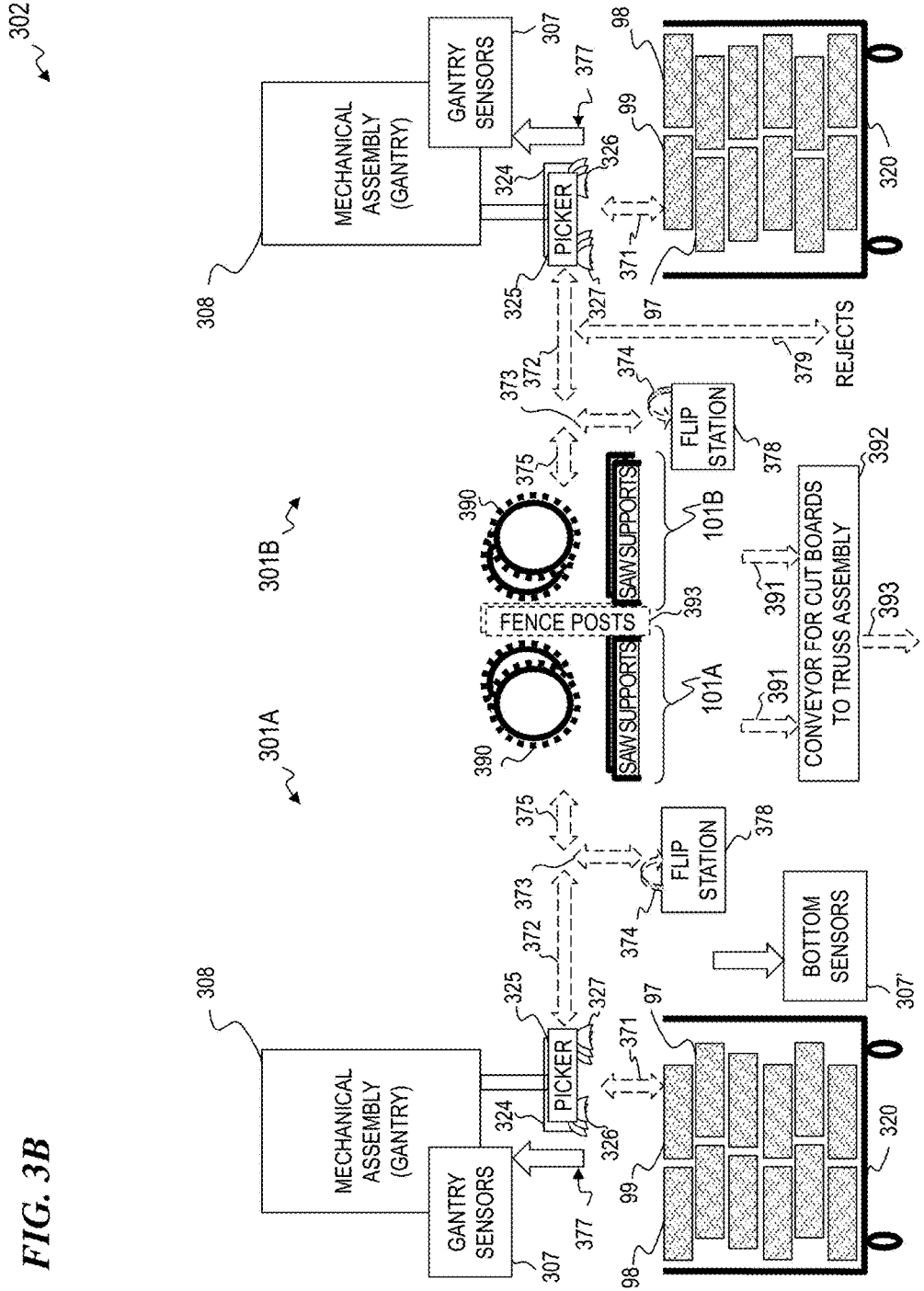
FIG. 3B is an end-view schematic diagram of multi-station lumber-cutting system 302, according to some embodiments of the present invention.

FIG. 3B is an end-view schematic diagram of lumber-cutting system 302, according to some embodiments of the present invention, which, for convenience, illustrates the processing of lumber where the lumber is moved left-to-right for the dual-saw lumber-picking-and-cutting system 301A and right-to-left for the dual-saw lumber-picking-and-cutting systems 301B in the FIG. 3B. In some embodiments, only top-side gantry-located sensors 307 are used, while in other embodiments, only bottom-side sensors 307' are used, while in yet other embodiments, both top-side gantry sensors 307 and bottom-side sensors 307' are used. In some embodiments, the mechanical assembly (e.g., the gantry) 308 has (in addition to the gantry sensors 307 if used) a single board-picker mechanism 325 that is used and carries one board at a time (from left-to-right in the FIG. 3B), while in other embodiments, gantry 308 has (in addition to the gantry sensors 307 if used) a plurality of board-picker mechanisms 324-325 that are each used to carry one or more boards at a time (from left-to-right in the FIG. 3B). In some embodiments, each of the plurality of board-picker mechanisms 324-325 uses staggered suction cups as described in co-pending U.S. patent application Ser. No. 15/426,966, filed Feb. 7, 2017 by Steven Weinschenk, titled "AUTOMATED SYSTEM AND METHOD FOR LUMBER PICKING," which is incorporated herein by reference. In some embodiments, gantry 308 is operable to pick one or more boards from each of one or more of a plurality of carts 320-321 (only two of which are shown here).

Continuing to refer to FIG. 3B, in some embodiments that use only top-side gantry-located sensors 307, a board 99 is scanned or imaged by gantry sensors 307 to determine the position and orientation of board 99 in absolute terms and/or in relation to other boards 97 and 98. In some embodiments, the points along the edges and top surface of board 99 are determined and distinguished by the height difference relative to the points detected of a lower board 97. In some embodiments, the points along the edges and top surface of board 99 are determined and distinguished by the brightness differences of the boards relative to the spaces between top board 99 and top board 98. In some embodiments, the points along the edges and top surface of board 99 obtained from top-side gantry-located sensors 307 are used to position picker(s) 324 and/or 325 in order to pick up board 99 (and/or simultaneously pick up board 98). Based on the geometry data obtained from the top-side gantry-located sensors 307, the board 99 is picked up by path 371, carried along path 372, possible dropped along path 379 to a rejection pile (in the case where system 302 and method 303 have determined that the current processing stations are not able to accommodate the detected flaws in the board), or deposited on flip station 378 by path 373 and/or taken to saw station 390 by path 375. In some embodiments, if the board is deposited on flip station 378, it is flipped over along path 374 (rotated 180 degrees around its long axis) and then the opposite side is inspected by gantry sensors 307 (or the board is picked up by picker(s) 324-325 and transported back over the bottom-side sensors 307' (only one set of possibly more than one are shown here) to perform the detailed inspection of the side not originally inspected during the first pass over sensors 307'), and based on the inspection of the opposite side, the now doubly-inspected board is dumped at the reject pile or transported and placed on saw station 390. In some embodiments, a conveyor 392 receives the cut boards (e.g., dropped via paths 391) and conveys the cut boards via path 393 to a truss-assembly table such as described in U.S. patent application Ser. No. 15/093,732 by Steven R. Weinschenk et al., titled "DIGITAL PROJECTION SYSTEM AND METHOD FOR WORKPIECE ASSEMBLY" which is incorporated herein by reference.

Figure 3C:
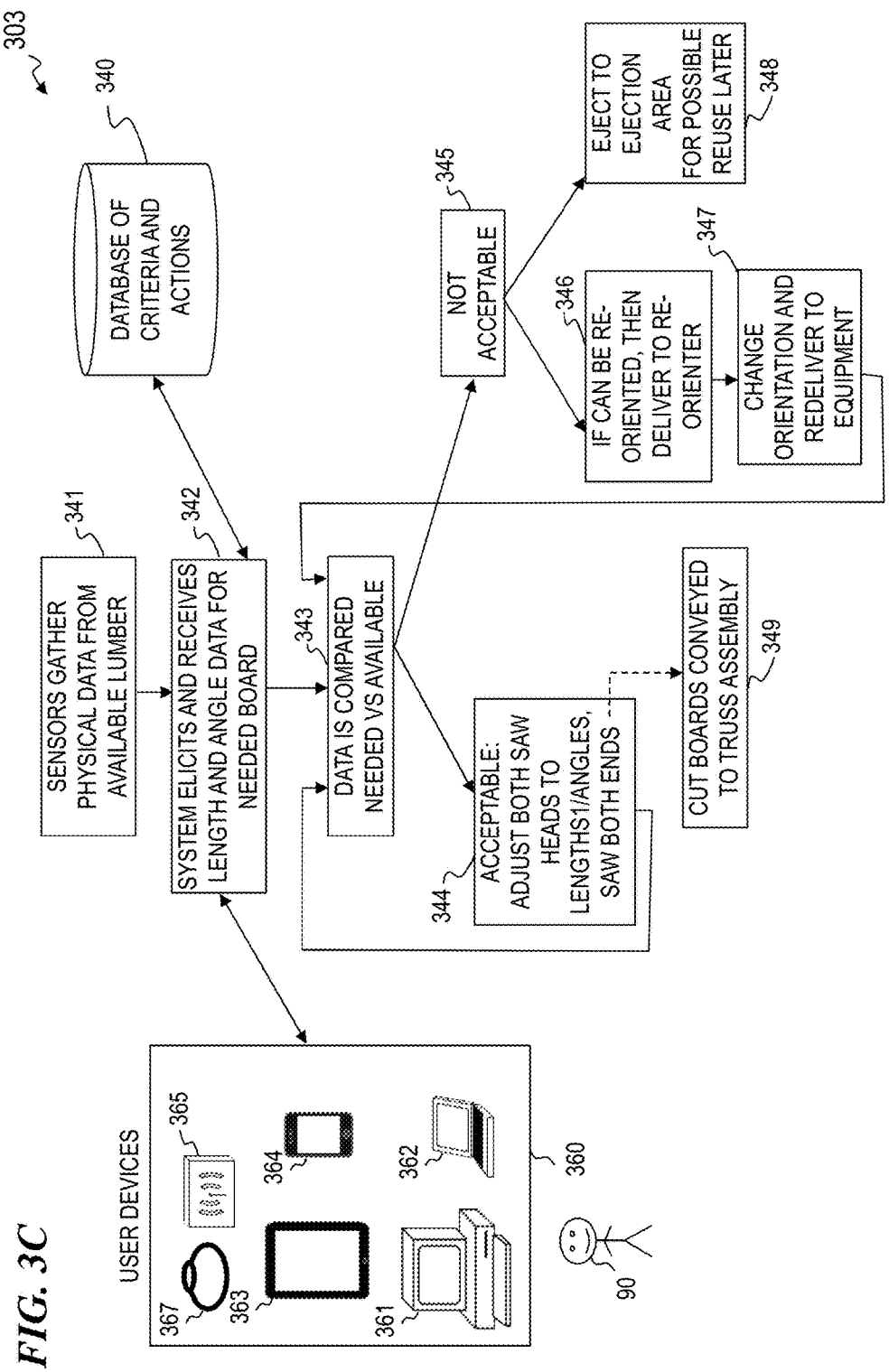
FIG. 3C is a flowchart of a method 303, according to some embodiments of the present invention.

FIG. 3C is a flowchart of a method 303, according to some embodiments of the present invention. In some embodiments of method 303, at block 341, the system (e.g., system 302 of FIG. 3A and FIG. 3B) gathers data from sensors as to dimensions, geometry (curvature), color and/or other attributes regarding a piece of available lumber (e.g., of a particular board 99). In some embodiments, at block 342, the system 302 elicits acceptable lumber data from a user 90 and/or from a stored set of data from database 340 that correlates characteristics of lumber with certain actions to be taken by the system, based on the end product to be built using the pieces of lumber. In some embodiments, system 302, using method 303, elicits and receives, from a human user 90 using one or more input/output devices 320, selection data that the system 302 uses to selects one or more sets of criteria and corresponding actions from a stored database that has been pre-loaded with a plurality of sets of criteria and corresponding actions that have been predetermined to meet requirements for each of a plurality of possible end products to be built using the pieces of lumber.

In some embodiments, the present invention utilizes one or more of the user devices 320 of each user 90, such as a desktop personal computer 361, laptop computer 362, tablet computer 363, smartphone 364, a position-sensing device 365 (which in some embodiments, is a stand-alone Global Positioning System (GPS) device (such as made by Garmin Ltd.) or in other embodiments, is part of a position-tracking system or another device such as a smartphone 364 or the like), and/or other devices such as wearable computers in clothing or smartwatches 367 or the like.

In some embodiments, the human user 90 or database 340 responds to the eliciting of information by indicating to system 302 which one of a plurality possible end-products is to be manufactured, wherein the criteria and actions for each respective end product is customized and optimized for that respective end product and stored in database 130, such that when an indication is received from the device 360 of user 90, that set of data is then used for the operations of blocks 343 through 349. In some embodiments, at block 341, sensors gather physical data from lumber. In some embodiments, distance data is received from each of one or more sensors for each of a plurality of point locations on one or more pieces of lumber. In some embodiments, those distance data are processed to obtain XYZ coordinates for each of the plurality of point locations, and curve-fitting algorithms are applied to find edges and surfaces of the one or more pieces of lumber, and determine the shapes and curves of edges and surfaces of the lumber. In some embodiments, at block 343, the physical geometric data is compared to the selected set of lumber parameters to obtain data comparison results. In some embodiments, at block 344, the data comparison results have been determined to be acceptable and therefore the piece of lumber is delivered to the saw station 390 where it is cut into boards having the desired lengths and end-angles for the end product being manufactured (such as, for example, a truss).

In some embodiments, at block 345, the data comparison results have been determined to be unacceptable. If the board is un-fixable (at least in regards to this particular station and the uses to which the lumber is to be applied in a commercially reasonable fashion), control is passed to block 348, and the piece of lumber is delivered to the rejection area. In some embodiments, at block 346, the piece of lumber is determined to be processable if reoriented, so that piece should be reoriented, so as a result the lumber is delivered to a reorienter. In some embodiments, at box 347, the orientation of the lumber is changed by the reorienter and then the now-reoriented piece of lumber is delivered to the processing equipment—so control passes to block 343 where data on the re0oriented board is again compared to the requirements of the truss parts being cut.

In some embodiments, system 302 uses its detection of the crown face (which typically has only one "high" point) of a crooked board to place the side opposite the crown face (which typically has two "high" points) against the saw fence of saw station so the board is more stable and does not move as the board is being sawed. Flip station 378 facilitates this positioning.

In some embodiments, system 302 uses method 303 (See FIG. 3C) to elicit and receive optical and/or XYZ point locations data (geometry data regarding the surfaces and edges of the lumber) to detect and measure wane or cracks on the board (see FIG. 2D). In some embodiments, system 301 detects cup defects (see FIG. 2F). In some embodiments, the system 302 detects crook defects (see FIG. 2A) and determines the crown face of the board. In some embodiments, system 302 further performs wane detection and/or split detection (see FIG. 2D), knot detection (see FIG. 2E), and/or bark detection (see FIG. 2D).

In some embodiments, system 302 detects other data (non-geometry data) such as grain quality and ring density. In some embodiments, these parameters are determined by one or more video cameras and one or more machine-vision algorithms applied to images obtained from the camera(s).

In some embodiments, system 302 reorients the lumber by physically flipping the lumber piece around its longest axes and/or rotating the lumber piece on one of its short axes to better optimize wood via mechanical action. In some embodiments, reorientation of the lumber is accomplished using compressed air; for example, by placing the piece of lumber on a surface (of flip station 378 of FIG. 3B) having a plurality of holes through which compressed air is selectively applied in a short burst along one edge to flip the board around its longest axis. In some other embodiments, reorientation of the lumber uses mechanical clamps or fasteners, such as a clamping device that grabs opposite faces of the piece of lumber, or a piercing device that screws or pierces to grab the lumber and flip the board around its longest axis.

In some embodiments, the method 303 and system 302, determine which ones (of a plurality of boards needed for one or more trusses being assembled on a neighboring truss assembly station) can be cut from the current board 99 on a saw station 390, and does cuts from one or both ends simultaneously. In some embodiments, it is the end boards that are cut off (e.g., boards 85, 86, 88, 89 of FIG. 1J)) and that drop to the conveyor that are the truss-member boards that are to be used (or that become unused scraps such as piece 87 of FIG. 1J), while the board 99 that remains on the support arms 118 is still raw stock that is yet to be cut to the final desired piece(s). In situations where one saw head 110 is first-arrived to be in position (for the desired length and angle) for a cut but the other saw head is still moving to its desired position, the earlier arriving saw head 110 will make its cut of its truss-member board (e.g., board 85 of FIG. 1J) and begin moving to position for the next cut, and when the latter-arriving saw head 110 later reaches its position (length and angle) for cutting the truss-member board from the opposite end of the source board 99, it will cut its opposite-end truss-member board (e.g., board 86 of FIG. 1J).

Figure 3D:
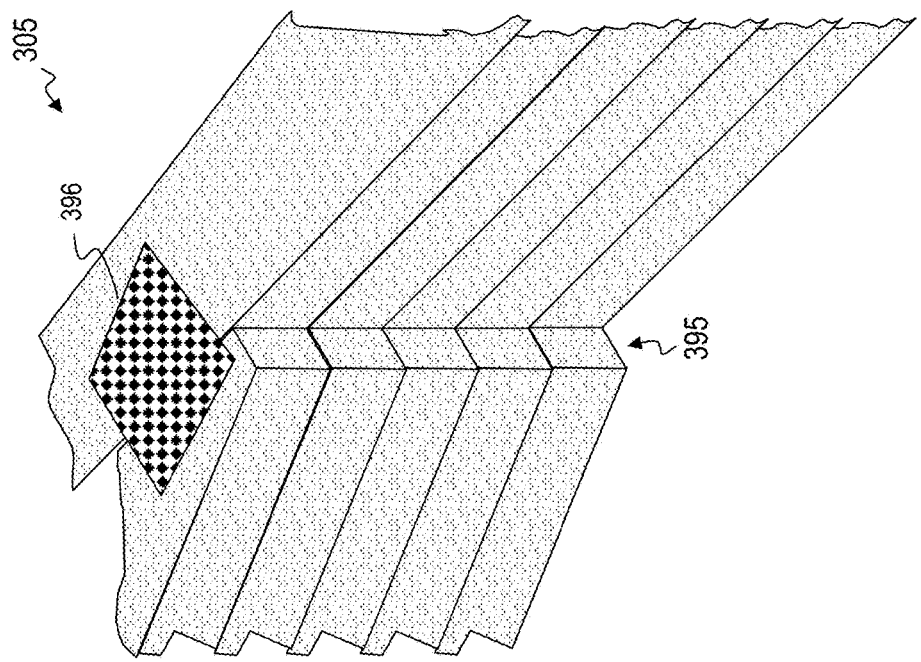
FIG. 3D is a diagram of a portion of a stack of trusses 304 that have uneven butt-end heights, which often results from conventional saw equipment.

FIG. 3D is a diagram of a portion of a stack of trusses 304, each having truss plates 396, that have uneven butt-end heights 394, which often results from conventional saw equipment.

Figure 3E:
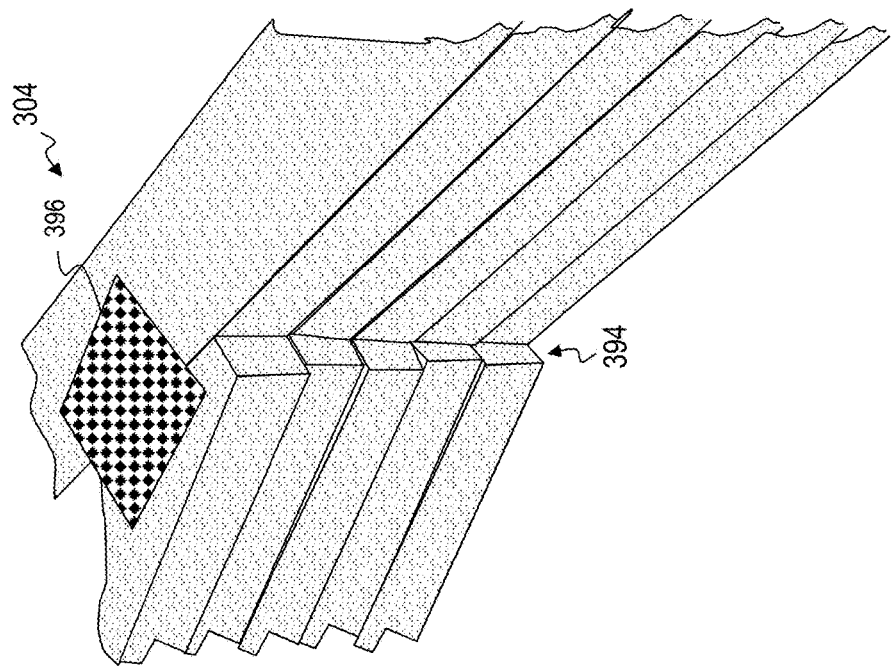
FIG. 3E is a diagram of a portion of a stack of trusses 305 that have even uniform butt-end heights, as a result of the more accurate end cut achievable from saw system 101 of the present invention.

FIG. 3E is a diagram of a portion of a stack of trusses 305 that have even uniform butt-end heights 395, as a result of the more accurate end cut achievable from saw system 101 of the present invention, which can move left-to-right and can rotate around a vertical axis defined by fence post rod 117 and support arb 118, in order to accurately cut a plurality of relatively short boards having a selected one of a plurality of different possible horizontal and/or vertical cut angles from a piece of lumber 99, according to some embodiments of the present invention.

Figure 4:
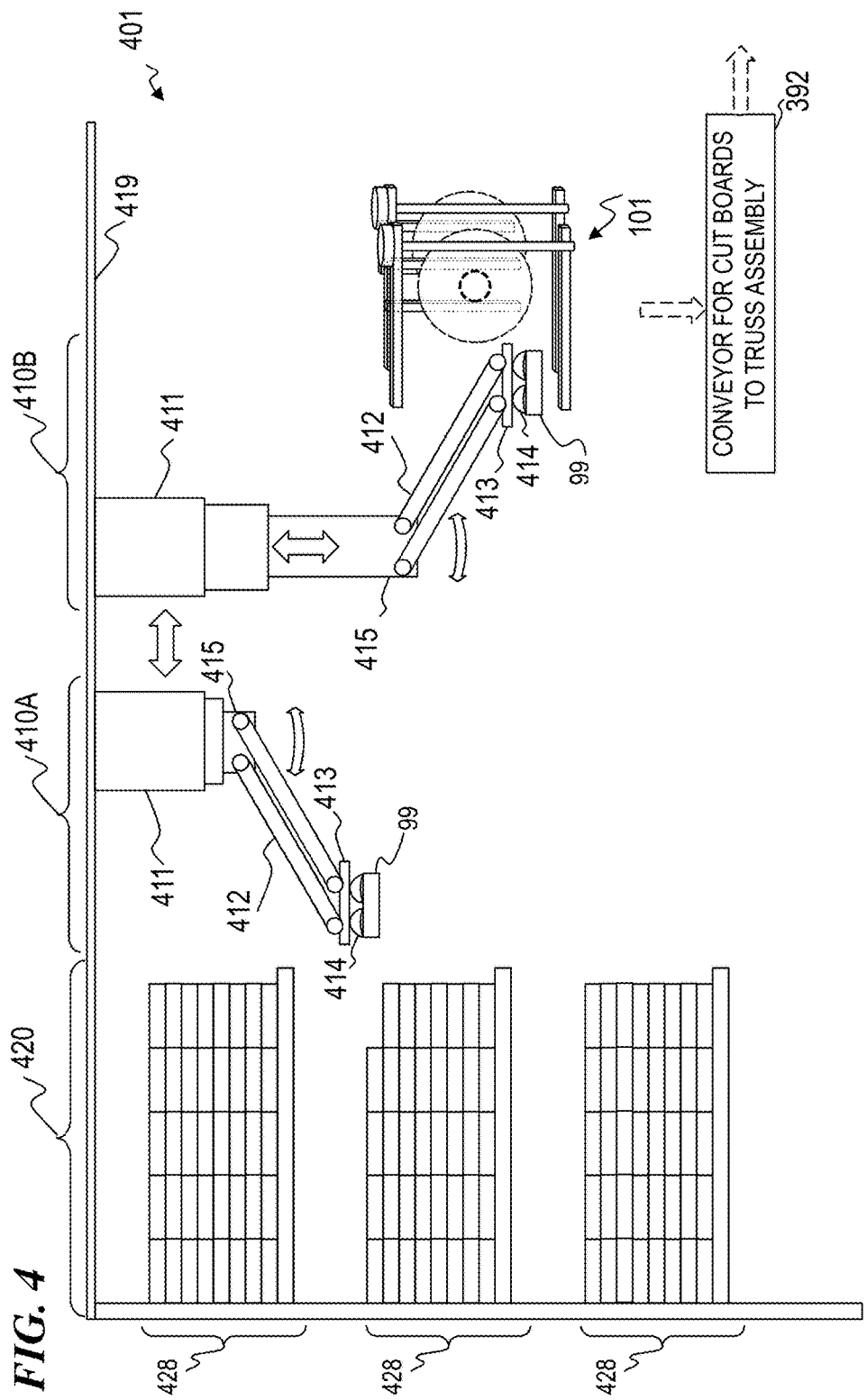
FIG. 4 is a side-view block diagram of a lumber-cutting system 401 that includes one or more lumber-transfer systems 410A, 410B, and a stacked-shelf lumber store 420, according to some embodiments of the present invention.

FIG. 4 is a side-view block diagram of a lumber-cutting system 401 that includes one or more lumber-transfer systems 410A, 410B, and a stacked-shelf lumber store 420, according to some embodiments of the present invention. In some embodiments, system 401 includes a plurality of lumber-transfer systems 410A, 410B, each running along a gantry track 419 between stacked-shelf lumber store 420 (e.g., in some embodiments, including a plurality of cantilevered board storage units 428 having shelves or arms that hold a stack of boards 99, In some embodiments, lumber-transfer systems 410A, 410B, each include an extendable column 411 having one or more extensions 415 that allow up-down movement control of swing arms 412 that allow picker head 413 (e.g., in some embodiments, having a plurality of controllable suction cups 414) to swing left into a cantilevered board storage unit 428 (above one shelf and below the one next higher) to pick up a board 99, then move rightward and swing to the right to place the board into saw system 101 (above board-support arms 118 and below the gantry tracks 190-see FIG. 1A)

Figure 5A:
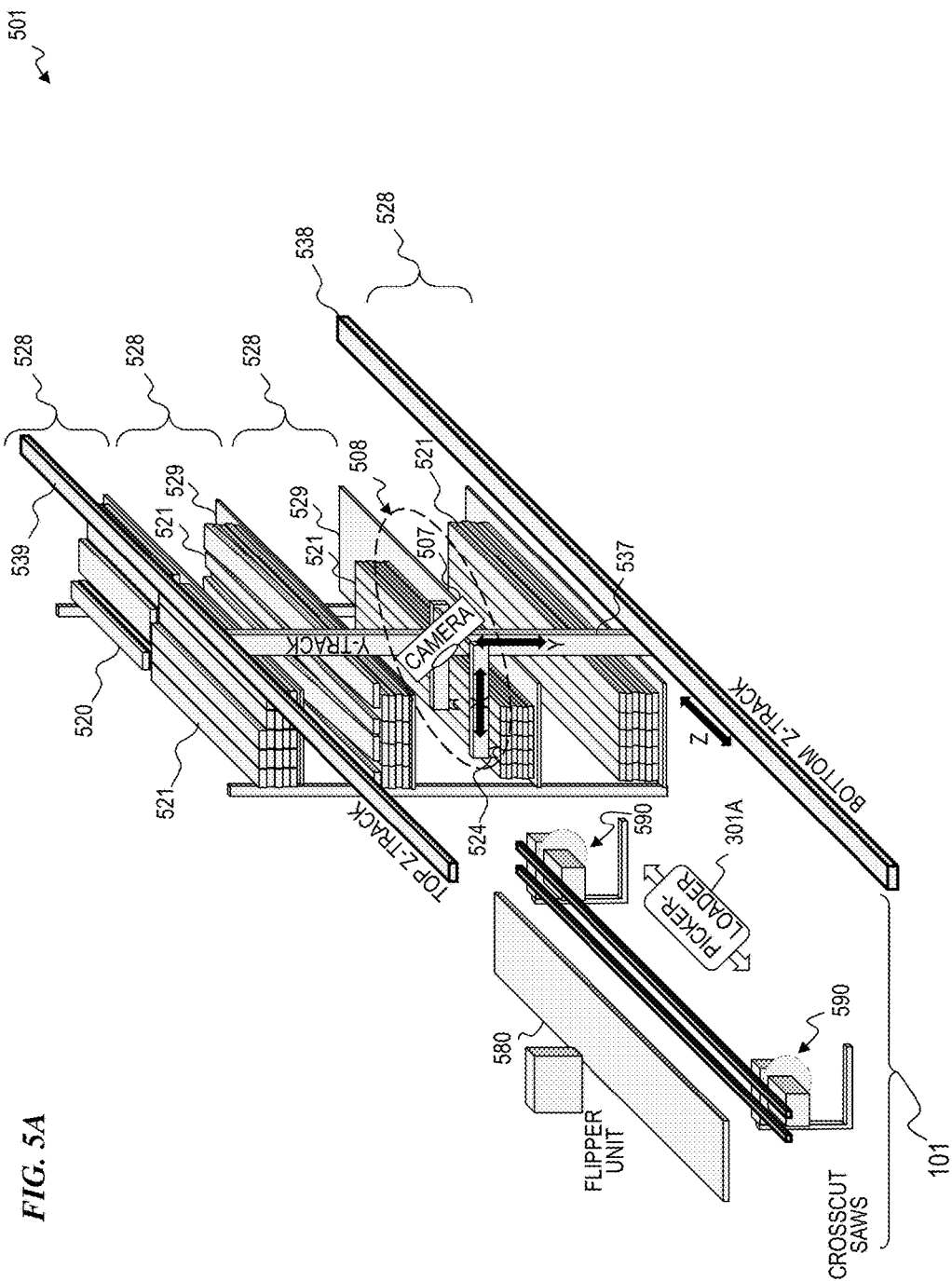
FIG. 5A is a perspective-view block diagram of a lumber-cutting system 501, according to some embodiments of the present invention.

FIG. 5A is a perspective-view block diagram of a lumber-cutting system 501, according to some embodiments of the present invention. In some embodiments, system 501 includes a gantry 508 that moves in and out relative to a plurality of stacks of lumber, each located on one of a plurality of bunks 528 (in the embodiment shown here, each bunk uses a shelf 529 to support its stack of lumber; in other embodiments, a plurality of cantilevered arms extending perpendicular to the long axes of the boards are spaced apart along the length of the boards and facilitate loading the bunks using a forklift or similar machinery). that are vertically displaced relative to one another. In some such embodiments, the picker 524 moves left-and-right relative to the figure to reach in above a selected one of the plurality of stacks of lumber 520-521, where one or more stacks of lumber 520-521 are placed on a plurality of vertically displaced shelves 529. A Y-track 537 is used to move the gantry 508 vertically to a selected one of the plurality of shelves 529 and its stack(s) of lumber 520-521, where a picker 524 (e.g., in some embodiments, using suction grippers) picks up a board that has been measured (as described above, for crook, bow, twist, cup, cracks and/or knots and the like), and delivered to saw system 390 and/or flipper 380 (e.g., in some embodiments, located vertically above saw system 390), or to the reject station (not shown). Thus, in some embodiments, gantry 508 moves up-down to one of plurality of stacked bunks (using shelves 529 or other suitable supports) of lumber stacks 520-521. Gantry 508 moves left-right over selected stack (e.g., 521) of lumber, picks a selected board 99, and camera/scanner 507 measures crown, bow, twist, wane, color, grade. Gantry 508 moves back-forth using tracks 538 and 539 between the stacked bunks 528 and saw input table of saw unit 390 (or flipper 380 or the discard pile of the reject unit).

Figure 5B:
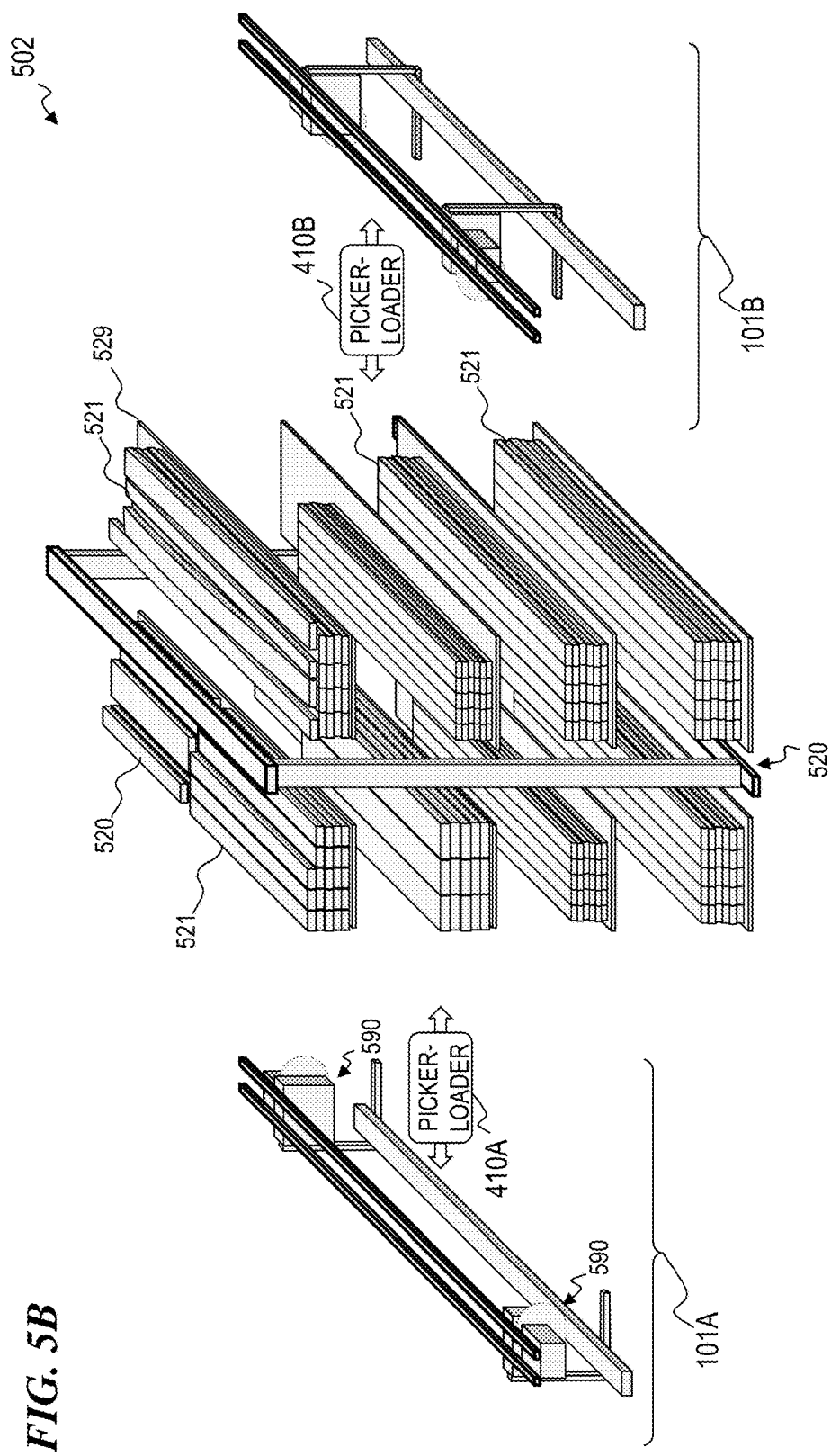
FIG. 5B is a perspective-view block diagram of a lumber-cutting system 502, according to some embodiments of the present invention.

FIG. 5B is a schematic diagram of a lumber-cutting system 502, according to some embodiments of the present invention. In some embodiments, system 502 is similar to system 501 described above, but has sets of bunks of lumber that are vertically displaced on both of the two sides of a centrally positioned gantry-movement system. Thus, in some embodiments, each lumber-transfer systems 410A, 410B moves up-down to one of plurality of stacked bunks (using shelves 529 or other suitable supports) of lumber stacks 520-521. Each lumber-transfer systems 410A, 410B moves left-right over selected stack (e.g., 521) of lumber, on the LEFT SIDE OR RIGHT SIDE of the central gantry-movement system 520, and picks a selected board 99, and camera/scanner 507 measures crown, bow, twist, wane, color, grade. Each lumber-transfer systems 410A, 410B moves back-forth between the two sets of stacked bunks and the selected saw input table of saw unit 101A or 101B (or a flipper 380 such as shown in FIG. 5A or the discard pile of the reject unit).

In some embodiments, the present invention provides an apparatus for sawing a first piece of lumber stock. This apparatus includes a first gantry structure having a length; a first plurality of saw heads including a first saw head having a blade and a second saw head having a blade; a first plurality of lumber supports including a first lumber support and a second lumber support, wherein the first lumber support and the second lumber support are configured to support the first piece of lumber stock; a plurality of actuators operably connected to the first gantry structure and to the first plurality of saw heads, and operably configured to move each one of the first plurality of saw heads and each one of the first plurality of lumber supports to a selected position of a plurality of positions along at least a portion of the length of the first gantry structure; and a saw controller operably connected to the plurality of actuators, and configured during a first period of time to move the first and second saw heads and the first and second lumber supports relative to the first piece of lumber stock as the first and second lumber supports support the first piece of lumber stock such that the first saw head and the first lumber support are located adjacent a first location along the first piece of lumber and the second saw head and the second lumber support are located adjacent a second location along the first piece of lumber, wherein the saw controller operates the first saw head to cut a first board off the first piece of lumber stock at the first location and the saw controller operates the second saw head to cut a second board off the first piece of lumber stock at the second location.

In some embodiments, the saw controller is configured during a second period of time to move the first and second saw heads and the first and second lumber supports relative to the first piece of lumber as the first and second lumber supports support the first piece of lumber such that the first saw head and the first lumber support are located at a third location along the first piece of lumber and the second saw head and the second lumber support are located at a fourth location along the first piece of lumber, wherein the saw controller operates the first saw head to cut a third board off the first piece of lumber stock and the saw controller operates the second saw head to cut a fourth board off the first piece of lumber stock.

In some embodiments, the first saw head and the first lumber support move together along the first gantry structure at a fixed spatial relationship to one another, and the second saw head and the second lumber support move together along the first gantry structure at a fixed spatial relationship to one another.

In some embodiments, the first saw head and the first lumber support move together along the first gantry structure at a fixed spatial relationship to one another and are configured to cut the first board off the first piece of lumber stock such that the blade of the first saw head cuts adjacent and parallel to a length of the first lumber support and such that the first lumber support continues to support the first piece of lumber stock that remains after the first board is cut off, and the second saw head and the second lumber support move together along the first gantry structure at a fixed spatial relationship to one another and are configured to cut the second board off the first piece of lumber stock such that the blade of the second saw head cuts adjacent and parallel to a length of the second lumber support and such that the second lumber support continues to support the first piece of lumber stock that remains after the second board is cut off.

In some embodiments, the first saw head and the first lumber support rotate together around a first vertical axis and move together along the first gantry structure at a fixed spatial relationship to one another and are configured to cut the first board off the first piece of lumber stock such that the blade of the first saw head cuts adjacent and parallel to a length of the first lumber support and such that the first lumber support continues to support the first piece of lumber stock that remains after the first board is cut off, and the second saw head and the second lumber support rotate together around a second vertical axis and move together along the first gantry structure at a fixed spatial relationship to one another and are configured to cut the second board off the first piece of lumber stock such that the blade of the second saw head cuts adjacent and parallel to a length of the second lumber support and such that the second lumber support continues to support the first piece of lumber stock that remains after the second board is cut off.

Some embodiments further include a first rotary actuator and a second rotary actuator operably connected to the saw controller; a first saw-fence post and a second saw-fence post, wherein the first saw head and the first lumber support are both connected to the first saw-fence post and the first rotary actuator is configured, under control of the saw controller, to rotate the first saw head and the first lumber support together around a vertical axis of the first saw-fence post, and wherein the second saw head and the second lumber support are both connected to the second saw-fence post and the second rotary actuator is configured, under control of the saw controller, to rotate the second saw head and the second lumber support together around a vertical axis of the second saw-fence post; and a board clamp operably connected to the saw controller and configured, under control of the saw controller, to urge the first piece of lumber stock against the first saw-fence post and the second saw-fence post while the first saw head cuts off the first board and the second saw head cuts off the second board.

Some embodiments further include a lumber pickup arm operatively coupled to the saw controller and configured to successively pick up at least one of a plurality of pieces of lumber stock from at least one source pile of pieces of lumber stock and to move the at least one piece of lumber stock in a direction substantially perpendicular to a long axis of the at least one piece of lumber stock and to deposit the at least one piece of lumber stock onto the first and second lumber support such that the board clamp can urge the at least one piece of lumber stock against the first saw-fence post and the second saw-fence post.

Some embodiments further include a lumber pickup arm operatively coupled to a raise/lower actuator of a second gantry structure, wherein the lumber pickup arm includes a first plurality of selectively air-pressure-activatable suction cups arranged in a staggered configuration; a first plurality of air valves operably connected to the first plurality of suction cups; an optical location device configured to generate location parameters for where the first piece of lumber is to be picked up; and a pickup controller operably connected to the first plurality of air valves and configured to control the raise/lower actuator to lower the lumber pickup arm based on the location parameters of where the first piece of lumber is to be picked up so that a first sub-plurality of the first plurality of suction cups seat on the first surface of the first piece of lumber, and to operate the first plurality of air valves so as to reduce air pressure in the first sub-plurality of the first plurality of suction cups to grab the first piece of lumber, wherein the pickup controller later increases air pressure in the plurality of the first plurality of suction cups to release the first piece of lumber.

In some embodiments, the present invention provides a method for sawing a first piece of lumber stock. This method includes: providing a first gantry structure having a length, a first plurality of saw heads supported by the first gantry structure including a first saw head having a blade and a second saw head having a blade, and a first plurality of lumber supports including a first lumber support and a second lumber support; supporting the first piece of lumber stock on the first lumber support and the second lumber support; moving, during a first period of time, the first and second saw heads and the first and second lumber supports relative to the first piece of lumber while supporting the first piece of lumber stock on the first and second lumber supports until the first saw head and the first lumber support are located adjacent a first location along the first piece of lumber and the second saw head and the second lumber support are located adjacent a second location along the first piece of lumber; and operating the first saw head to cut a first board off the first piece of lumber stock at the first location and operating the second saw head to cut a second board off the first piece of lumber stock at the second location.

Some embodiments of the method further include moving, during a second period of time, the first and second saw heads and the first and second lumber supports relative to the first piece of lumber while supporting the first piece of lumber on the first and second lumber supports until the first saw head and the first lumber support are located at a third location along the first piece of lumber and the second saw head and the second lumber support are located at a fourth location along the first piece of lumber; and operating the first saw head to cut a third board off the first piece of lumber stock at the third location and operating the second saw head to cut a fourth board off the first piece of lumber stock at the fourth location.

In some embodiments of the method, the moving of the first saw head and the first lumber support is done such that the first saw head and the first lumber support move together along the first gantry structure at a fixed spatial relationship to one another, and the moving of the second saw head and the second lumber support is done such that the second saw head and the second lumber support move together along the first gantry structure at a fixed spatial relationship to one another.

In some embodiments of the method, the moving of the first saw head and the first lumber support is done such that the first saw head and the first lumber support move together along the first gantry structure at a fixed spatial relationship to one another and cut the first board off the first piece of lumber stock such that the blade of the first saw head cuts adjacent and parallel to a length of the first lumber support and such that the first lumber support continues to support the first piece of lumber stock remaining after the first board is cut off, and the moving of the second saw head and the second lumber support is done such that the second saw head and the second lumber support move together along the first gantry structure at a fixed spatial relationship to one another and cut the second board off the first piece of lumber stock such that the blade of the second saw head cuts adjacent and parallel to a length of the second lumber support and such that the second lumber support continues to support the first piece of lumber stock remaining after the second board is cut off.

In some embodiments of the method, the first saw head and the first lumber support rotate together around a first vertical axis and move together along the first gantry structure at a fixed spatial relationship to one another and cut the first board off the first piece of lumber stock such that the blade of the first saw head cuts adjacent and parallel to a length of the first lumber support and such that the first lumber support continues to support the first piece of lumber stock remaining after the first board is cut off, and the second saw head and the second lumber support rotate together around a second vertical axis and move together along the first gantry structure at a fixed spatial relationship to one another and cut the second board off the first piece of lumber stock such that the blade of the second saw head cuts adjacent and parallel to a length of the second lumber support and such that the second lumber support continues to support the first piece of lumber stock remaining after the second board is cut off.

Some embodiments of the method further include a first saw-fence post and a second saw-fence post, wherein the first saw head and the first lumber support are both connected to the first saw-fence post and wherein the second saw head and the second lumber support are both connected to the second saw-fence post; rotating the first saw head and the first lumber support together around a vertical axis of the first saw-fence post; rotating the second saw head and the second lumber support together around a vertical axis of the second saw-fence post; and urging the first piece of lumber stock against the first saw-fence post and the second saw-fence post while the first saw head cuts off the first board and the second saw head cuts off the second board.

Some embodiments of the method further include providing a lumber pickup arm; successively picking up at least one of a plurality of pieces of lumber stock from at least one source pile of pieces of lumber stock; moving the at least one piece of lumber stock in a direction substantially perpendicular to a long axis of the at least one piece of lumber stock; depositing the at least one piece of lumber stock onto the first and second lumber support; and urging the at least one piece of lumber stock against the first saw-fence post and the second saw-fence post.

Some embodiments of the method further include providing a lumber pickup arm operatively coupled to a second gantry structure, wherein the lumber pickup arm includes a first plurality of selectively air-pressure-activatable suction cups arranged in a staggered configuration; generating location parameters for where the first piece of lumber is to be picked up; and lowering the lumber pickup arm based on the location parameters of where the first piece of lumber is to be picked up so that a first sub-plurality of the first plurality of suction cups seat on the first surface of the first piece of lumber, and reducing air pressure in the first sub-plurality of the first plurality of suction cups to grab the first piece of lumber, and later increasing air pressure in the plurality of the first plurality of suction cups to release the first piece of lumber.

In some embodiments, the present invention provides an apparatus for sawing a first piece of lumber stock. This apparatus includes a first gantry structure having a length, a first plurality of saw heads supported by the first gantry structure including a first saw head having a blade and a second saw head having a blade; first means for supporting the first piece of lumber stock at a first location along a length of the first piece of lumber stock; second means for supporting the first piece of lumber stock at a second location along a length of the first piece of lumber stock; means for moving, during a first period of time, the first and second saw heads and the first and second lumber supports relative to the first piece of lumber while supporting the first piece of lumber stock until the first saw head and the first means for supporting are located adjacent a first location along the first piece of lumber and the second saw head and the second means for supporting are located adjacent a second location along the first piece of lumber; and means for operating the first saw head to cut a first board off the first piece of lumber stock at the first location and means for operating the second saw head to cut a second board off the first piece of lumber stock at the second location.

Some embodiments further include means for moving, during a second period of time, the first and second saw heads and the first and second lumber supports relative to the first piece of lumber while supporting the first piece of lumber on the first and second lumber supports until the first saw head and the first lumber support are located at a third location along the first piece of lumber and the second saw head and the second lumber support are located at a fourth location along the first piece of lumber; and means for operating the first saw head to cut a third board off the first piece of lumber stock at the third location and operating the second saw head to cut a fourth board off the first piece of lumber stock at the fourth location.

Some embodiments further include a lumber pickup arm; means for successively picking up at least one of a plurality of pieces of lumber stock from at least one source pile of pieces of lumber stock; means for moving the at least one piece of lumber stock in a direction substantially perpendicular to a long axis of the at least one piece of lumber stock; means for depositing the at least one piece of lumber stock onto the first and second lumber support; and means for urging the at least one piece of lumber stock against the first saw-fence post and the second saw-fence post.

Some embodiments further include a lumber pickup arm operatively coupled to a second gantry structure, wherein the lumber pickup arm includes a first plurality of selectively air-pressure-activatable suction cups arranged in a staggered configuration; means for generating location parameters for where the first piece of lumber is to be picked up; and means for lowering the lumber pickup arm based on the location parameters of where the first piece of lumber is to be picked up so that a first sub-plurality of the first plurality of suction cups seat on the first surface of the first piece of lumber, and reducing air pressure in the first sub-plurality of the first plurality of suction cups to grab the first piece of lumber, and later increasing air pressure in the plurality of the first plurality of suction cups to release the first piece of lumber.

In the exemplary embodiments here, various combinations of elements are described. Unless specifically indicated otherwise, no element is considered to be critical and one or more of the example elements may be optionally omitted. Further, it is specifically contemplated that various combinations of the various simple embodiments separately described herein may be implemented as a more complex combination of elements to implement the present invention. Further still, it is specifically contemplated that various combinations of the patents and patent applications cited herein may be combined with one or more of the various simple embodiments separately described herein to obtain a more complex combination of elements to implement the present invention.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for sawing a first piece of lumber stock, the apparatus comprising:
    a first gantry structure having a length;
    a first plurality of saw heads including a first saw head having a blade and a second saw head having a blade;
    a first plurality of lumber supports including a first lumber support and a second lumber support, wherein the first lumber support and the second lumber support are configured to support the first piece of lumber stock;
    a plurality of actuators operably connected to the first gantry structure and to the first plurality of saw heads, and operably configured to move each one of the first plurality of saw heads and each one of the first plurality of lumber supports to a selected position of a plurality of positions along at least a portion of the length of the first gantry structure; and
    a saw controller operably connected to the plurality of actuators, and configured during a first period of time to move the first and second saw heads and the first and second lumber supports relative to the first piece of lumber stock as the first and second lumber supports support the first piece of lumber stock such that the first saw head and the first lumber support are located adjacent a first location along the first piece of lumber and the second saw head and the second lumber support are located adjacent a second location along the first piece of lumber, wherein the saw controller operates the first saw head to cut a first board off the first piece of lumber stock at the first location and the saw controller operates the second saw head to cut a second board off the first piece of lumber stock at the second location.

2. The apparatus of claim 1, wherein the saw controller is configured during a second period of time to move the first and second saw heads and the first and second lumber supports relative to the first piece of lumber as the first and second lumber supports support the first piece of lumber such that the first saw head and the first lumber support are located at a third location along the first piece of lumber and the second saw head and the second lumber support are located at a fourth location along the first piece of lumber, wherein the saw controller operates the first saw head to cut a third board off the first piece of lumber stock and the saw controller operates the second saw head to cut a fourth board off the first piece of lumber stock.

3. The apparatus of claim 1,
    wherein the first saw head and the first lumber support move together along the first gantry structure at a fixed spatial relationship to one another, and
    wherein the second saw head and the second lumber support move together along the first gantry structure at a fixed spatial relationship to one another.

4. The apparatus of claim 1,
    wherein the first saw head and the first lumber support move together along the first gantry structure at a fixed spatial relationship to one another and are configured to cut the first board off the first piece of lumber stock such that the blade of the first saw head cuts adjacent and parallel to a length of the first lumber support and such that the first lumber support continues to support the first piece of lumber stock that remains after the first board is cut off, and wherein the second saw head and the second lumber support move together along the first gantry structure at a fixed spatial relationship to one another and are configured to cut the second board off the first piece of lumber stock such that the blade of the second saw head cuts adjacent and parallel to a length of the second lumber support and such that the second lumber support continues to support the first piece of lumber stock that remains after the second board is cut off.

5. The apparatus of claim 1, wherein the first saw head and the first lumber support rotate together around a first vertical axis and move together along the first gantry structure at a fixed spatial relationship to one another and are configured to cut the first board off the first piece of lumber stock such that the blade of the first saw head cuts adjacent and parallel to a length of the first lumber support and such that the first lumber support continues to support the first piece of lumber stock that remains after the first board is cut off, and wherein the second saw head and the second lumber support rotate together around a second vertical axis and move together along the first gantry structure at a fixed spatial relationship to one another and are configured to cut the second board off the first piece of lumber stock such that the blade of the second saw head cuts adjacent and parallel to a length of the second lumber support and such that the second lumber support continues to support the first piece of lumber stock that remains after the second board is cut off.

6. The apparatus of claim 1, further comprising:

a first rotary actuator and a second rotary actuator operably connected to the saw controller;

a first saw-fence post and a second saw-fence post, wherein the first saw head and the first lumber support are both connected to the first saw-fence post and the first rotary actuator is configured, under control of the saw controller, to rotate the first saw head and the first lumber support together around a vertical axis of the first saw-fence post, and wherein the second saw head and the second lumber support are both connected to the second saw-fence post and the second rotary actuator is configured, under control of the saw controller, to rotate the second saw head and the second lumber support together around a vertical axis of the second saw-fence post; and a board clamp operably connected to the saw controller and configured, under control of the saw controller, to urge the first piece of lumber stock against the first saw-fence post and the second saw-fence post while the first saw head cuts off the first board and the second saw head cuts off the second board.

7. The apparatus of claim 6, further comprising:

a lumber pickup arm operatively coupled to the saw controller and configured to successively pick up at least one of a plurality of pieces of lumber stock from at least one source pile of pieces of lumber stock and to move the at least one piece of lumber stock in a direction substantially perpendicular to a long axis of the at least one piece of lumber stock and to deposit the at least one piece of lumber stock onto the first and second lumber support such that the board clamp can urge the at least one piece of lumber stock against the first saw-fence post and the second saw-fence post.

8. The apparatus of claim 6, further comprising:

a lumber pickup arm operatively coupled to a raise/lower actuator of a second gantry structure, wherein the lumber pickup arm includes a first plurality of selectively air-pressure-activatable suction cups arranged in a staggered configuration;

a first plurality of air valves operably connected to the first plurality of suction cups;

an optical location device configured to generate location parameters for where the first piece of lumber is to be picked up; and a pickup controller operably connected to the first plurality of air valves and configured to control the raise/lower actuator to lower the lumber pickup arm based on the location parameters of where the first piece of lumber is to be picked up so that a first sub-plurality of the first plurality of suction cups seat on the first surface of the first piece of lumber, and to operate the first plurality of air valves so as to reduce air pressure in the first sub-plurality of the first plurality of suction cups to grab the first piece of lumber, wherein the pickup controller later increases air pressure in the plurality of the first plurality of suction cups to release the first piece of lumber.

9. A method for sawing a first piece of lumber stock, the method comprising:

providing a first gantry structure having a length, a first plurality of saw heads supported by the first gantry structure including a first saw head having a blade and a second saw head having a blade, and a first plurality of lumber supports including a first lumber support and a second lumber support;

supporting the first piece of lumber stock on the first lumber support and the second lumber support;

moving, during a first period of time, the first and second saw heads and the first and second lumber supports relative to the first piece of lumber while supporting the first piece of lumber stock on the first and second lumber supports until the first saw head and the first lumber support are located adjacent a first location along the first piece of lumber and the second saw head and the second lumber support are located adjacent a second location along the first piece of lumber; and operating the first saw head to cut a first board off the first piece of lumber stock at the first location and operating the second saw head to cut a second board off the first piece of lumber stock at the second location.

10. The method of claim 9, further comprising:

moving, during a second period of time, the first and second saw heads and the first and second lumber supports relative to the first piece of lumber while supporting the first piece of lumber on the first and second lumber supports until the first saw head and the first lumber support are located at a third location along the first piece of lumber and the second saw head and the second lumber support are located at a fourth location along the first piece of lumber; and operating the first saw head to cut a third board off the first piece of lumber stock at the third location and operating the second saw head to cut a fourth board off the first piece of lumber stock at the fourth location.

11. The method of claim 9, wherein the moving of the first saw head and the first lumber support is done such that the first saw head and the first lumber support move together along the first gantry structure at a fixed spatial relationship to one another, and wherein the moving of the second saw head and the second lumber support is done such that the second saw head and the second lumber support move together along the first gantry structure at a fixed spatial relationship to one another.

12. The method of claim 9,
wherein the moving of the first saw head and the first lumber support is done such that the first saw head and the first lumber support move together along the first gantry structure at a fixed spatial relationship to one another and cut the first board off the first piece of lumber stock such that the blade of the first saw head cuts adjacent and parallel to a length of the first lumber support and such that the first lumber support continues to support the first piece of lumber stock remaining after the first board is cut off, and wherein the moving of the second saw head and the second lumber support is done such that the second saw head and the second lumber support move together along the first gantry structure at a fixed spatial relationship to one another and cut the second board off the first piece of lumber stock such that the blade of the second saw head cuts adjacent and parallel to a length of the second lumber support and such that the second lumber support continues to support the first piece of lumber stock remaining after the second board is cut off.

13. The method of claim 9,
wherein the first saw head and the first lumber support rotate together around a first vertical axis and move together along the first gantry structure at a fixed spatial relationship to one another and cut the first board off the first piece of lumber stock such that the blade of the first saw head cuts adjacent and parallel to a length of the first lumber support and such that the first lumber support continues to support the first piece of lumber stock remaining after the first board is cut off, and wherein the second saw head and the second lumber support rotate together around a second vertical axis and move together along the first gantry structure at a fixed spatial relationship to one another and cut the second board off the first piece of lumber stock such that the blade of the second saw head cuts adjacent and parallel to a length of the second lumber support and such that the second lumber support continues to support the first piece of lumber stock remaining after the second board is cut off.

14. The method of claim 9, further comprising:
providing a first saw-fence post and a second saw-fence post, wherein the first saw head and the first lumber support are both connected to the first saw-fence post and wherein the second saw head and the second lumber support are both connected to the second saw-fence post;

rotating the first saw head and the first lumber support together around a vertical axis of the first saw-fence post;

rotating the second saw head and the second lumber support together around a vertical axis of the second saw-fence post; and urging the first piece of lumber stock against the first saw-fence post and the second saw-fence post while the first saw head cuts off the first board and the second saw head cuts off the second board.

15. The method of claim 14, further comprising:
providing a lumber pickup arm;

successively picking up at least one of a plurality of pieces of lumber stock from at least one source pile of pieces of lumber stock;

moving the at least one piece of lumber stock in a direction substantially perpendicular to a long axis of the at least one piece of lumber stock;

depositing the at least one piece of lumber stock onto the first and second lumber support; and urging the at least one piece of lumber stock against the first saw-fence post and the second saw-fence post.

16. The method of claim 14, further comprising:
providing a lumber pickup arm operatively coupled to a second gantry structure, wherein the lumber pickup arm includes a first plurality of selectively air-pressure-activatable suction cups arranged in a staggered configuration;

generating location parameters for where the first piece of lumber is to be picked up; and lowering the lumber pickup arm based on the location parameters of where the first piece of lumber is to be picked up so that a first sub-plurality of the first plurality of suction cups seat on the first surface of the first piece of lumber, and reducing air pressure in the first sub-plurality of the first plurality of suction cups to grab the first piece of lumber, and later increasing air pressure in the plurality of the first plurality of suction cups to release the first piece of lumber.

17. An apparatus for sawing a first piece of lumber stock, the method comprising:
a first gantry structure having a length, a first plurality of saw heads supported by the first gantry structure including a first saw head having a blade and a second saw head having a blade;

first means for supporting the first piece of lumber stock at a first location along a length of the first piece of lumber stock;

second means for supporting the first piece of lumber stock at a second location along a length of the first piece of lumber stock;

means for moving, during a first period of time, the first and second saw heads and the first and second lumber supports relative to the first piece of lumber while supporting the first piece of lumber stock until the first saw head and the first means for supporting are located adjacent a first location along the first piece of lumber and the second saw head and the second means for supporting are located adjacent a second location along the first piece of lumber; and means for operating the first saw head to cut a first board off the first piece of lumber stock at the first location and means for operating the second saw head to cut a second board off the first piece of lumber stock at the second location.

18. The apparatus of claim 17, further comprising:
means for moving, during a second period of time, the first and second saw heads and the first and second lumber supports relative to the first piece of lumber while supporting the first piece of lumber on the first and second lumber supports until the first saw head and the first lumber support are located at a third location along the first piece of lumber and the second saw head and the second lumber support are located at a fourth location along the first piece of lumber; and means for operating the first saw head to cut a third board off the first piece of lumber stock at the third location and operating the second saw head to cut a fourth board off the first piece of lumber stock at the fourth location.

19. The apparatus of claim 17, further comprising:
a lumber pickup arm;
means for successively picking up at least one of a plurality of pieces of lumber stock from at least one source pile of pieces of lumber stock;
means for moving the at least one piece of lumber stock in a direction substantially perpendicular to a long axis of the at least one piece of lumber stock;
means for depositing the at least one piece of lumber stock onto the first and second lumber support; and
means for urging the at least one piece of lumber stock against the first saw-fence post and the second saw-fence post.

20. The apparatus of claim 17, further comprising:
a lumber pickup arm operatively coupled to a second gantry structure, wherein the lumber pickup arm includes a first plurality of selectively air-pressure-activatable suction cups arranged in a staggered configuration;
means for generating location parameters for where the first piece of lumber is to be picked up; and
means for lowering the lumber pickup arm based on the location parameters of where the first piece of lumber is to be picked up so that a first sub-plurality of the first plurality of suction cups seat on the first surface of the first piece of lumber, and reducing air pressure in the first sub-plurality of the first plurality of suction cups to grab the first piece of lumber, and later increasing air pressure in the plurality of the first plurality of suction cups to release the first piece of lumber.

* * * * *